(12) United States Patent
Ramos Maza

(10) Patent No.: US 8,956,393 B2
(45) Date of Patent: Feb. 17, 2015

(54) DEVICES, SYSTEMS, AND METHODS FOR ACETABULUM REPAIR

(76) Inventor: Luis Edgardo Ramos Maza, Mexico City (MX)

( * ) Notice: Subject to any disclaimer, the term of this patent is extended or adjusted under 35 U.S.C. 154(b) by 252 days.

(21) Appl. No.: 12/831,249

(22) Filed: Jul. 6, 2010

(65) Prior Publication Data

US 2012/0010617 A1  Jan. 12, 2012

(51) Int. Cl.
*A61B 17/80* (2006.01)
*A61B 17/17* (2006.01)
*A61B 17/86* (2006.01)
*A61B 17/88* (2006.01)

(52) U.S. Cl.
CPC ......... *A61B 17/8066* (2013.01); *A61B 17/1746* (2013.01); *A61B 17/8685* (2013.01); *A61B 17/8861* (2013.01); *A61B 17/8085* (2013.01); *A61B 17/864* (2013.01)
USPC ............. 606/286; 606/70; 606/287; 606/289; 606/297

(58) Field of Classification Search
USPC .................................. 606/286, 287, 289, 291
See application file for complete search history.

(56) References Cited

U.S. PATENT DOCUMENTS

| 4,454,876 | A | 6/1984 | Mears |
| 4,573,458 | A | 3/1986 | Lower |
| 4,800,874 | A | 1/1989 | David et al. |
| 5,108,397 | A | 4/1992 | White |
| 5,336,224 | A | 8/1994 | Selman |
| 5,527,310 | A | 6/1996 | Cole et al. |
| 5,569,253 | A | 10/1996 | Farris et al. |
| 5,785,712 | A * | 7/1998 | Runciman et al. ............ 606/283 |
| 6,004,353 | A | 12/1999 | Masini |
| 6,302,887 | B1 * | 10/2001 | Spranza et al. ............... 606/916 |
| 6,340,362 | B1 | 1/2002 | Pierer et al. |
| 6,440,131 | B1 | 8/2002 | Haidukewych |
| 6,706,046 | B2 | 3/2004 | Orbay et al. |
| 2004/0030336 | A1* | 2/2004 | Khanna ........................... 606/61 |
| 2005/0096657 | A1* | 5/2005 | Autericque et al. ............ 606/69 |
| 2005/0165401 | A1 | 7/2005 | Pack |
| 2006/0276896 | A1 | 12/2006 | Fallin et al. |
| 2007/0225714 | A1 | 9/2007 | Gradl |
| 2008/0077133 | A1 | 3/2008 | Schulze |

(Continued)

FOREIGN PATENT DOCUMENTS

| CN | 201085674 Y | 7/2008 |
| CN | 101427949 A | 5/2009 |

(Continued)

OTHER PUBLICATIONS

John H. Harris, Jr., et al.: "Acetabular Fractures Revisited: Part I, Redefinition of the Letournel Anterior Column," American Journal of Roentgenology, 2004, No. 182, pp. 1363-1366.

(Continued)

*Primary Examiner* — Andrew Yang
*Assistant Examiner* — Olivia C Chang
(74) *Attorney, Agent, or Firm* — Baker & Hostetler LLP

(57) ABSTRACT

Systems for repairing acetabulum fractures can include a bone plate that has openings therein and one or more bolts sized to fit through the openings. The bone plate can cooperate with the head portions of the bolts to prevent them from spinning within the holes as screws are attached to the bolts. Such arrangements can assist in reverse implantation methods in which the bone plate is introduced into the true pelvis of a patient.

12 Claims, 23 Drawing Sheets

(56) References Cited

U.S. PATENT DOCUMENTS

2008/0108989 A1 5/2008 Parsell et al.
2008/0234676 A1 9/2008 Schulze et al.
2009/0287214 A1 11/2009 Yu
2009/0326541 A1 12/2009 Metzinger et al.
2010/0023016 A1 1/2010 Botimer

FOREIGN PATENT DOCUMENTS

| WO | 01/05315 A1 | 1/2001 |
| WO | 2004/107957 A2 | 12/2004 |
| WO | 2006/009795 A1 | 1/2006 |
| WO | 2009/073466 A1 | 6/2009 |
| WO | 2012/054105 A2 | 4/2012 |

OTHER PUBLICATIONS

Dean Thornton, MD: "Acetabulum, Fractures," eMedicine Radiology, 2009.
Qureshi AA et al.: "Infrapectineal plating for acetabular fractures: a technical adjunct to internal fixation," Journal of Orthopaedic Trauma, Mar. 2004, vol. 3.
International Search Report and Written Opinion, issued in related application No. PCT/US2011/042992 on May 21, 2012.
G. Yves et al.: "Isolated quadrilateral plate fracture: an unusual acetabular fracture," Canadian Medical Association, vol. 52, No. 5, Oct. 2009.
M.E. Muller, et al.: "3.5 mm Quadrilateral Surface Places Technique Guide," Manual of Internal Fixation, 3rd Edition. Berlin: Springer-Verlag. 1991.

* cited by examiner

DEVICES, SYSTEMS, AND METHODS FOR ACETABULUM REPAIR

TECHNICAL FIELD

The present disclosure relates to devices, systems, and methods that may be used to repair acetabulum fractures.

BRIEF DESCRIPTION OF THE DRAWINGS

The written disclosure describes illustrative embodiments that are non-limiting and non-exhaustive. Reference is made to certain of such illustrative embodiments that are depicted in the figures, in which.

DETAILED DESCRIPTION

Figure 1:
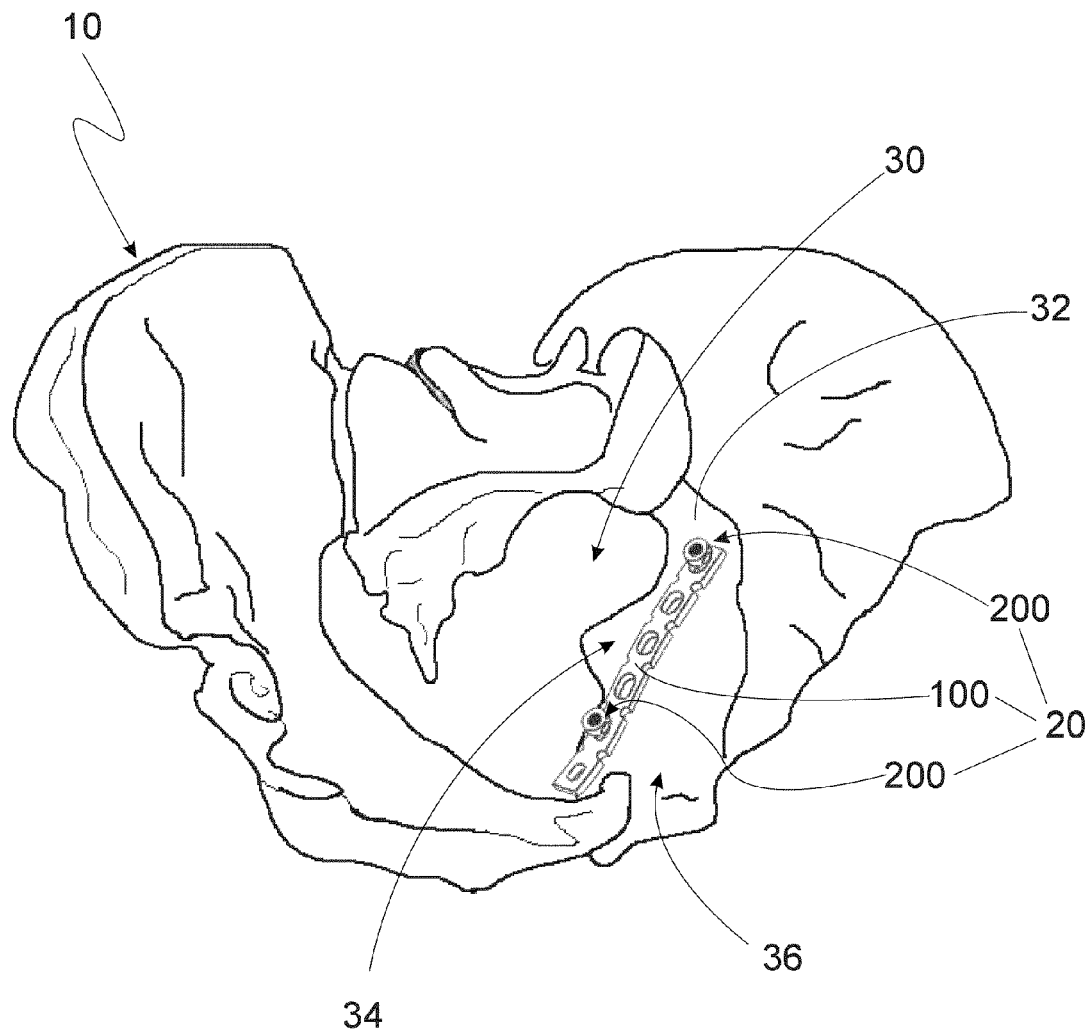
FIG. 1 is a perspective view of an embodiment of a fixation system that includes a bone plate, wherein the bone plate has been implanted in a substantially vertical orientation relative to a posterior column of a pelvis.

The acetabulum is a concave surface of the pelvis into which the head of the femur is received to form the hip joint. Fractures of the acetabulum are injuries that are generally complicated to repair for a variety of reasons. For example, such fractures often result from high-energy trauma, the configuration and location of the acetabulum and its surrounding structures are complex, and a large number of important soft-tissue structures (e.g., nerves, vessels, the bladder, sex organs, etc.) are situated nearby. Associated fracture traces, fragments, and displacements can be complicated, such that it is extremely difficult to rebuild the original bone structures.

Traditional approaches to acetabulum repair generally use large incisions, some of which may be about 20 to about 50 centimeters in length. Such incisions expose important anatomical structures, which can be damaged during the repair procedures. The traditional approaches can be lengthy, result in large amounts of blood loss, have a high risk of wound infection, injure important soft tissues, and/or result in heterotopic ossification.

Additionally, many current implants are placed either dorsally or in a suprapectineal position. Dorsally placed implants are generally used to repair transverse fractures. For these procedures, it is generally necessary to cut out lateral rotator muscles in order to expose the acetabulum, and the sciatic nerve can be damaged in the process.

Suprapectineal implants may be used for medial displacements. For standard procedures, reduction is performed using large or invasive instruments. Moreover, bone fragments are pulled in a direction that is opposite from the direction in which the fragments have been displaced. For example, screws can be placed in a standard 3.5 millimeter reconstruction plate, which is placed over the displaced bone at a position that is opposite from the direction in which the bone has been displaced. While suprapectineal placement of a medial plate may work well for cranial displacements of the anterior column, it can be less desirable for certain medial displacements of the anterior and posterior columns. For example, suprapectineal or extra-pelvic plates can, in some instances, only use screws from above in order to prevent new displacements of the fragments.

Another common approach for fixing medially displaced fragments is to use "spring plates," which are created by bending a thin, tubular plate in an "L" shape. The tubular plate is placed beneath a suprapectineal plate and is fixed at a position that is distanced from the fracture site. The tubular plate thus extends to the infrapectinal position and acts as a spring, without any infrapectineal fixation, in order to reduce the medially displaced fragments. In this approach, the medially displaced fragments are not directly reduced by the infrapectinal plates, but rather, the infrapectinal plates that are connected to the fragments are pushed to a more lateral position, thereby indirectly reducing the fragment. This is a difficult approach for fracture reduction and fixation, since the system acts in directions that are not directly opposed to the forces that would act to displace the fragments.

Infrapectineal plates may also be implanted using the so-called Stoppa approach, in which a surgeon stands at a position that is opposite of the acetabular fracture in order to achieve a standard fixation of plates in an infrapectineal position. The approach uses an incision that can be about 20 centimeters in length and that is a great distance from the acetabulum itself. One major drawback of this approach is the necessity to pull the femoral vein medially in order to reach the acetabulum. Additionally, while the Stoppa approach may be feasible for fixation of a dorsal part of an infrapectineal plate, it is extremely difficult and risky for fixation of a ventral part of the plate due to the direction in which drilling is performed.

Various embodiments disclosed herein can reduce or eliminate one or more drawbacks of the approaches to acetabulum repair discussed above. For example, some embodiments can repair acetabular injuries using minimally invasive surgery, which can, in further embodiments, reduce the size of an incision site from a typical length of about 20 to 50 centimeters down to about 7 to 10 centimeters. Also, as a result of the use of a smaller incision, the resulting scar can be smaller, which can be more aesthetically pleasing to the patient and can heal quicker and less painfully. Certain embodiments can reduce trauma to a patient, thereby allowing the patient to recover more quickly, and may result in less blood loss during the procedure itself, thereby eliminating or reducing the blood transfusions. Moreover, intrapelvic plates are fixed in infrapectineal positions (e.g., are implanted within, or at an interior of, the true pelvis) so as to act directly against forces that produce fragment displacements. One or more of the foregoing advantages and/or other advantages of various embodiments disclosed herein may be specifically discussed hereafter or may otherwise be apparent to those of skill in the art based on the present disclosure.

FIG. 1 illustrates a pelvis 10 to which a fixation system 20 has been attached. The fixation system includes a bone plate 100 and a plurality of bolts 200 that extend through the bone plate 100. The fixation system further includes separate screws (not shown) that are advanced through an exterior surface of the pelvis 10 and coupled with each bolt 200. The bone plate 100 may be said to be fixed to the pelvis 10 in a reverse manner. Otherwise stated, the bone plate 100 is positioned within the true pelvis 30. More specifically, the bone plate 100 is positioned against an interior surface 32 of the pelvis 10 that extends along the posterior column 34 and, in the illustrated embodiment, in a relatively vertical direction. Depending on the type of fracture involved, the bone plate 100 may instead extend between the posterior column 34 and the anterior column 36, such as, for example, in a substantially horizontal orientation (see FIG. 27).

The bone plate 100 and the bolts 200, along with systems and methods for their implantation, are discussed in detail below. In some embodiments, a hole is drilled through the pelvis 10 from an exterior surface to the interior surface 32. The bone plate 100 is inserted into the interior of the true pelvis 30 and placed against the interior surface 32. The bolt 200 is inserted through the bone plate 100 and into the hole in the pelvic bone from the interior direction. A screw is inserted into the hole in the pelvic bone from the exterior side of the bone and is received within a shaft of the bolt 200 (see FIG. 25). The screw is tightened so as to anchor the bone plate 100 in place. Two or more pairs of bolts 200 and screws can be used to reduce the fractured bone into the proper orientation and for fixation of the bone.

Figure 2:
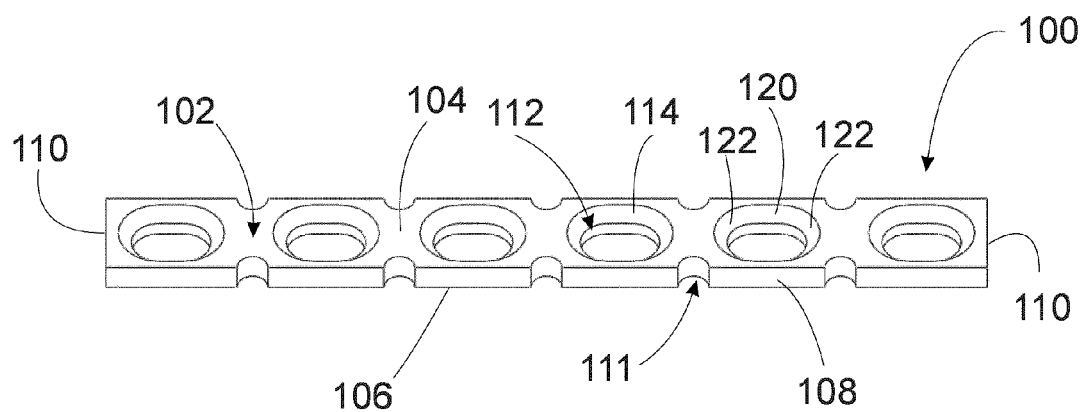
FIG. 2 is a perspective view of an embodiment of a bone plate.
Figure 3:
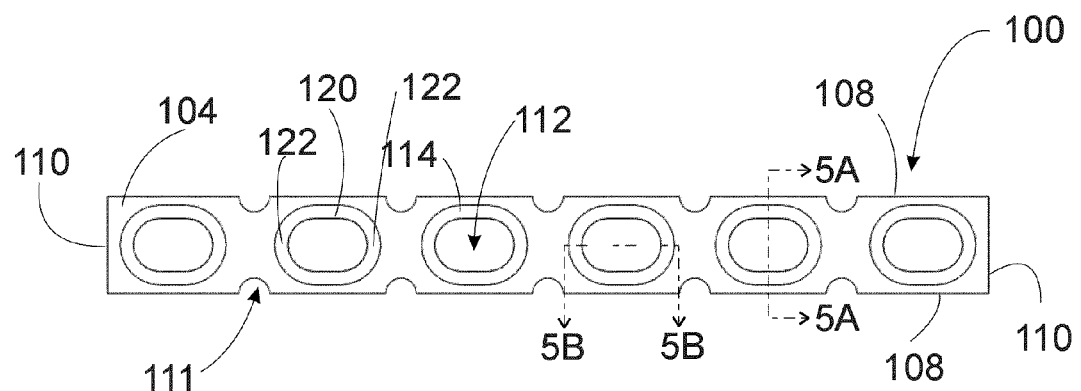
FIG. 3 is a top plan view of the bone plate of FIG. 2.
Figure 4:
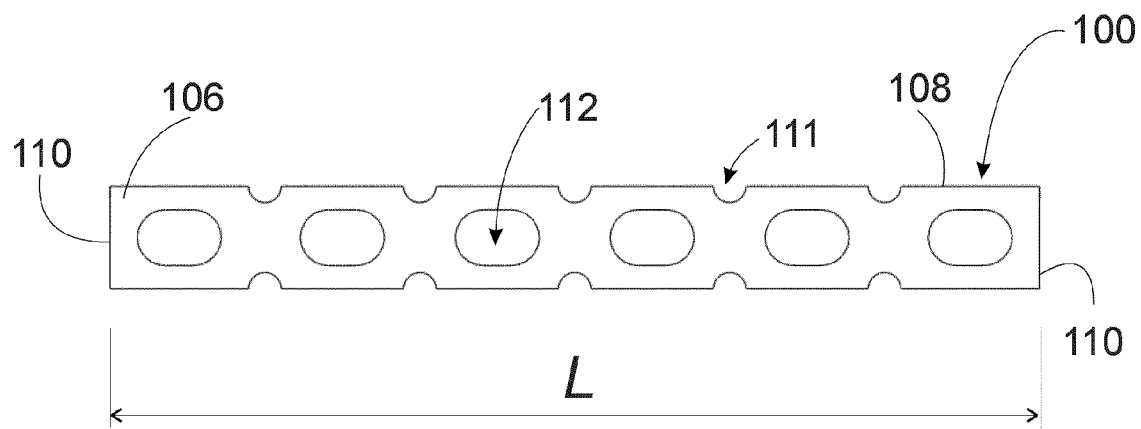
FIG. 4 is a bottom plan view of the bone plate of FIG. 2.

FIGS. 2-4 illustrate an embodiment of the bone plate 100, which also may be referred to as an intrapelvic plate or as an infrapectineal plate. The bone plate 100 is shown in an unformed, original, or pre-use orientation. As further discussed below, the bone plate 100 can be reconfigured to a shaped or implantation configuration, such as the contoured configuration shown in FIG. 1. The bone plate 100 can include a body 102 that defines an upper face 104 and a lower face 106. In the illustrated embodiment, when the bone plate 100 is in the original orientation, the upper and lower faces 104, 106 are substantially planar and are substantially parallel to each other. The bone plate 100 can be configured such that the lower face 106 is placed adjacent to the interior surface 32 of the pelvis 10 for implantation.

The bone plate 100 can include side faces 108 and end faces 110 that extend between the upper and lower faces 104, 106. In the illustrated embodiment, the end faces 110 are substantially planar. The side faces 108 include substantially planar regions that are separated from each other by a series of notches 111. The notches 111 extend inwardly toward a longitudinal axis of the bone plate 100. In the illustrated embodiment, the notches 111 of the opposing side faces 108 can extend toward one another. In the illustrated embodiment, the upper and lower faces 104, 106, the side faces 108, and the end faces 110 form pointed corners. In other embodiments, the corners and/or edges at which the upper and lower faces 104, 106, the side faces 108, and the end faces 110 meet can be rounded.

The bone plate 100 can further include a plurality of openings 112 that extend through the body 102 and that are each defined at an outer edge thereof by a sidewall 114. As further discussed below, the sidewall 114 can be configured to permit translational motion of a bolt 200 therein yet can prevent rotational motion of the bolt 200 relative thereto, which can assist with implantation of the bone plate 100.

In some embodiments, the sidewalls 114 are shaped such that the openings 112 are oblong, with a longer dimension in a longitudinal direction (e.g., in a direction of elongation of the bone plate 100) than in a transverse direction (e.g., in a direction perpendicular to the direction of elongation of the bone plate 100 and extending between the side faces 108). Specifically, in the illustrated embodiment, each sidewall 114 defines a pair of opposing anti-rotation surfaces 120 that extend in the longitudinal direction. The anti-rotation surfaces 120 are joined at either end thereof by rounded end surfaces 122.

Figure 5A:
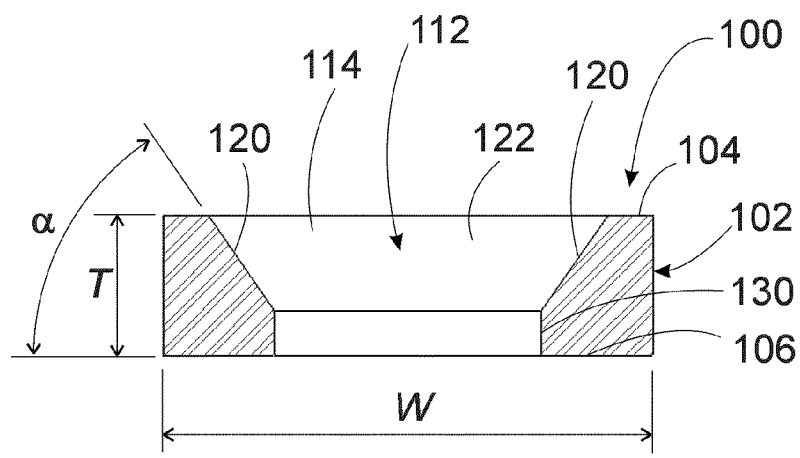
FIG. 5A is a cross-sectional view of the bone plate of FIG. 2 taken along the view line 5A-5A in FIG. 3.

With reference to FIGS. 2, 3, and 5A, the anti-rotation surfaces 120 of the illustrated embodiment are substantially planar, defining a substantially linear cross-section that extends along the longitudinal direction. As shown in FIG. 5A, the planar anti-rotation surfaces 120 can define an angle α relative to the lower face 106, which is discussed further below. In some embodiments, the anti-rotation surfaces 120 extend fully from the upper face 104 to the lower face 106. However, in the illustrated embodiment, the anti-rotation surfaces 120 extend from the upper face 104 to a lower rim 130, and the rim 130 extends to the lower face 106. The rim 130 can be substantially perpendicular to the lower face 106, and can provide a reinforcing thickness at the lower end of the body 102. The lower end of the body 102 that defines a periphery of the opening 112 thus can be less susceptible to possible damage or deformation when a bolt 200 is inserted through the opening 112. In various embodiments, a height of the rim 130 is no greater than about ⅓, ¼, ⅕, 1/10, 1/20, or 1/30 of a total thickness T of the body 102.

Figure 5B:
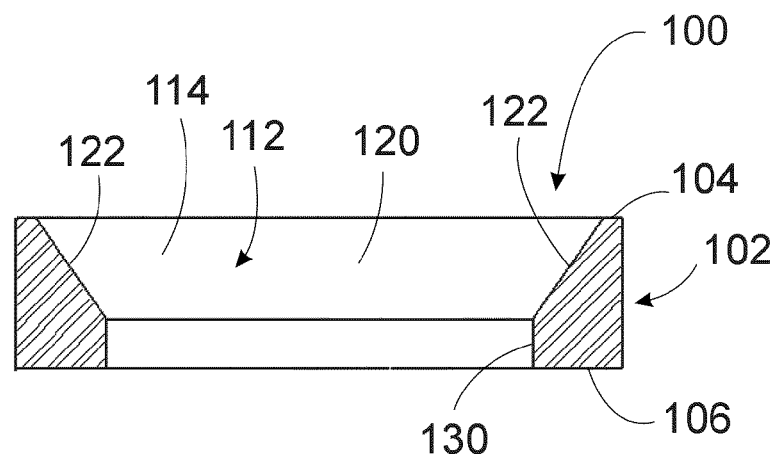
FIG. 5B is a cross-sectional view of the bone plate of FIG. 1 taken along the view line 5B-5B in FIG. 3.

As shown in FIG. 5B, the sidewall 114 also can define a substantially linear profile at the end surface 122. Other arrangements are also possible.

Figure 6A:
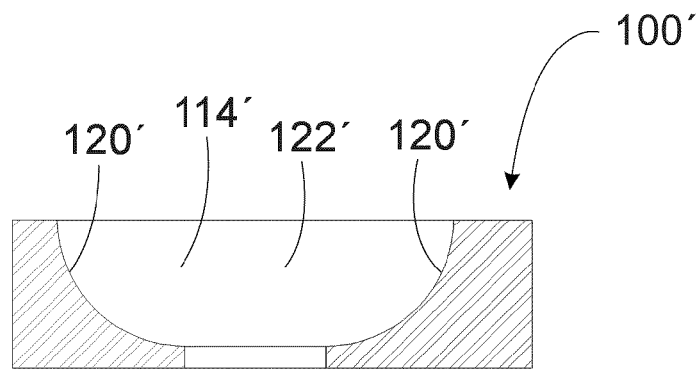
FIG. 6A is a cross-sectional view of another embodiment of a bone plate taken along a view line such as the view line 5A-5A in FIG. 3.
Figure 6B:
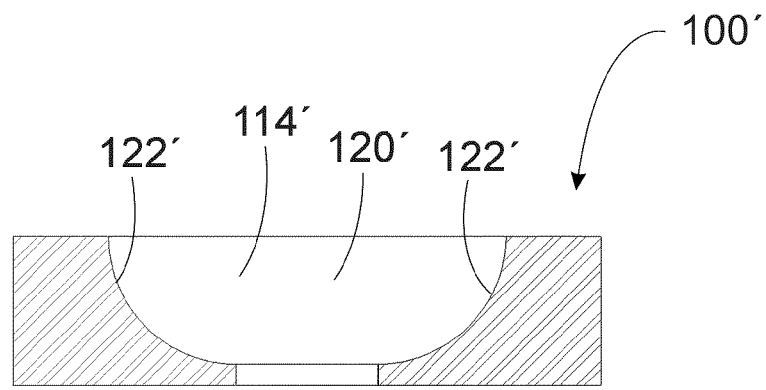
FIG. 6B is a cross-sectional view of the bone plate of FIG. 6A taken along a view line such as the view line 5B-5B in FIG. 3.

FIGS. 6A and 6B illustrate cross-sectional views of another embodiment of a bone plate 100', which resembles the bone plate 100, but includes a sidewall 114' that defines a different cross-sectional profile. In particular, the bone plate 100' includes anti-rotation surfaces 120' that have a substantially parabolic profile. The sidewall 114' can include end surfaces 122' that likewise are substantially parabolic. The bone plate 100' is discussed further below.

With reference again to FIGS. 2-4, the openings 112 can be aligned in a single row along a longitudinal axis of the bone plate 100, and the notches 111 can be positioned longitudinally between adjacent openings 112. The notches 111 can reduce resistance of the bone plate 100 to torsion that can bend or deform the bone plate 100 from the pre-use configuration to the implantation configuration. In some embodiments, the bone plate 100 comprises a unitary piece of material, and the notches 111 can increase the pliability of the bone plate 100 in the longitudinal and transverse directions, as well as in a direction perpendicular to each of the longitudinal and transverse directions (e.g., a direction normal to the upper face 104). The bone plate 100 can be formed of one or more materials that are able to maintain the new implantation configuration once the bone plate 100 has been moved thereto. For example, in some embodiments, the bone plate 100 comprises one or more of stainless steel, titanium, cobalt chrome, and combinations thereof. In various embodiments, pliers, a bending press, and/or a practitioner's hands (unaided by instruments in some embodiments) can be used to transition the bone plate 100 from the pre-use configuration (which may be substantially planar) to the implantation configuration (which may be contoured to an inner surface of the pelvis). Once in the implantation configuration, the bone plate 100 can be inserted into a patient, and can maintain the implantation configuration so as to reduce bone fragments into proper alignment.

In other embodiments, the side faces 108 of the bone plate body 102 can more closely follow a contour of the openings 112 such that, rather than defining planar faces between adjacent notches 111, the side faces 108 define surfaces that are convexly rounded so as to roughly follow the contour of the openings 112 between adjacent notches 111. Such an arrangement may increase the pliability of the bone plate 100.

Dimensions of the bone plate 100 (i.e., its length L, width W, and/or thickness T) and/or the shape thereof can be configured for placement within the true pelvis of a patient. For example, the bone plate 100 can be sized so as to be placed in a substantially vertical orientation along an inner surface of the posterior column 34 of the pelvis 10 (see FIG. 1). As another example, the bone plate 100 can be sized so as to be placed in a substantially horizontal (or ventral-to-dorsal) orientation that extends along an inner surface of the pelvis 10 from the anterior column 36 to the posterior column 34 (see FIG. 27). In some embodiments, a single bone plate 100 may be configured for used in either the vertical or horizontal orientation. One or more of the dimensions of the bone plate 100, as well as the material of which the bone plate 100 is composed, likewise may be selected to achieve a desired malleability and/or rigidity. In various embodiments, the length L of the bone plate 100 is within a range of from about 80 to about 120 millimeters, from about 90 to about 110 millimeters, or from about 95 to about 105 millimeters; is no more than about 80, 90, 95, 100, 105, 110, or 115 millimeters; or is no less than about 80, 90, 95, 100, 105, 110, or 115 millimeters. In some embodiments, the length is about 105 millimeters. In various embodiments, the width W of the bone plate 100 is within a range of from about 8 to about 15 millimeters or within a range of from about 10 to about 11 millimeters; is no more than about 8, 10, or 12 millimeters; or is no less than about 8, 10, or 12 millimeters. In some embodiments, the width is about 10.2 millimeters. In various embodiments, the thickness T of the bone plate 100 is within a range of from about 1 millimeter to about 10 millimeters, from about 2 millimeters to about 8 millimeters, or from about 3 millimeters to about 5 millimeters; is no more than about 10 millimeters, no more than about 5 millimeters, or no more than about 4 millimeters; or is no less than about 2 millimeters, no less than about 3 millimeters, or no less than about 5 millimeters. In some embodiments, the thickness is about 3.2 millimeters.

The number and/or shapes of the openings 112 likewise can be selected based on the desired performance characteristics of the bone plate 100. The illustrated embodiment includes six openings 112, but more or fewer openings 112 may be desirable. For example, the number of openings 112 and/or a longitudinal length of the bone plate 100 can vary depending on the target site of the bone plate 100. In the illustrated embodiment, a length of the openings 112 at an upper end thereof is about 11.5 millimeters and a width at the upper end is about 7.8 millimeters, whereas a length of the openings 112 at a lower end thereof is about 9.0 millimeters and a width at the lower end is about 6.0 millimeters. While inventive aspects may lie in the measurements and ranges described herein, other values may be used in other embodiments.

Figure 7:
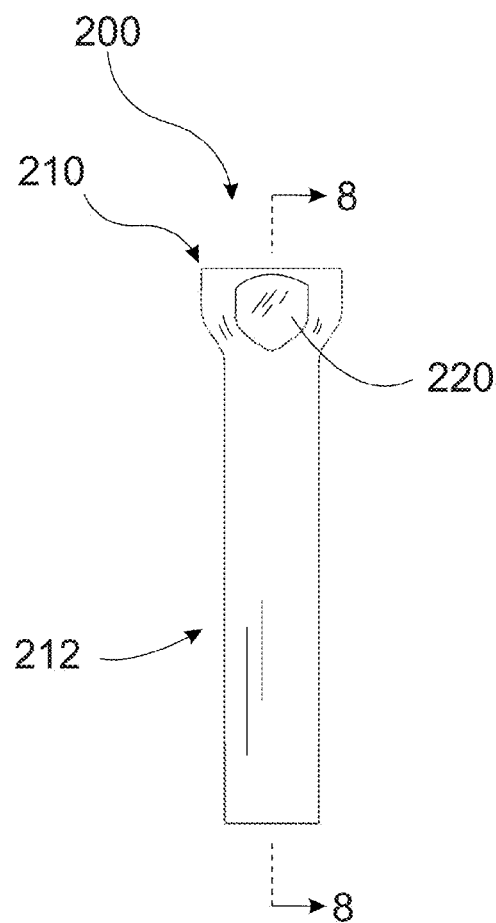
FIG. 7 is a perspective view of an embodiment of a bolt.
Figure 8:
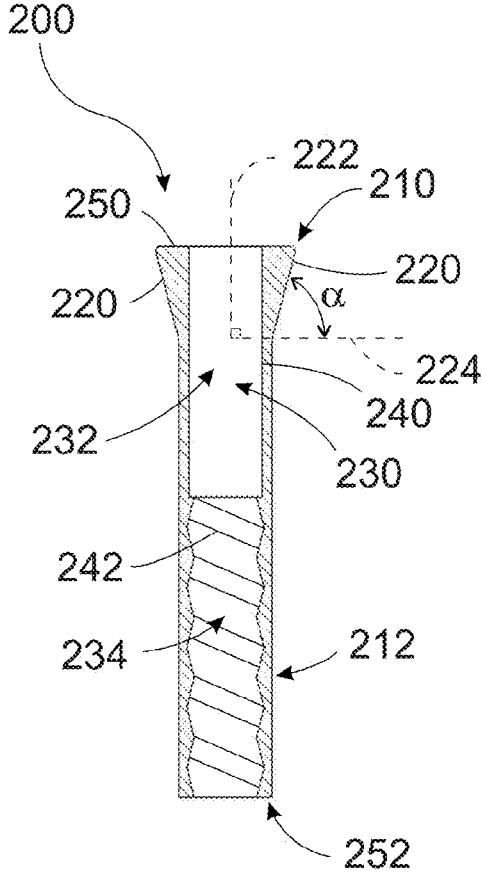
FIG. 8 is a cross-sectional view of the bolt of FIG. 7 taken along the view line 8-8 in FIG. 7.

FIGS. 7 and 8 illustrate an embodiment of a cannulated bolt 200 that is configured to cooperate with any of the sidewalls 114 of the bone plate 100 during installation of the bone plate 100. The cannulated bolt 200 may also be referred to as a Chicago bolt or sex bolt. The bolt 200 can comprise any suitable material, such as, for example, one or more of stainless steel, titanium, cobalt chrome, and combinations thereof. In some embodiments, at least a portion of the bolt 200 can desirably be radio opaque. The bolt 200 can include a head 210 and a hollow shaft 212.

In some embodiments, the head 210 can be sized to be fully seated with the bone plate 100 such that a proximal face 250 thereof is even with or is recessed relative to the upper face 104 of the bone plate 100. The head 210 can include one or more anti-rotation surfaces 220, which can be configured to cooperate with the anti-rotation surfaces 120 of the sidewalls 114 of the bone plate 100 to prevent rotation of the bolt 200 within an opening 112 about a longitudinal axis 222 of the bolt 200. In the illustrated embodiment, the anti-rotation surfaces 220 are at opposite sides of the head 210. The anti-rotation surfaces 220 are substantially planar and are complementary to the planar anti-rotation surfaces 120 of the embodiment of the bone plate illustrated in FIGS. 5A and 5B. The anti-rotation surfaces 220 can be angled relative to a plane 224 that is perpendicular to the longitudinal axis 222 of the bolt 200. In the illustrated embodiment, each anti-rotation surface 220 defines an angle α relative to the plane 224.

With reference again to FIG. 5A, the angle α defined by the anti-rotation surfaces 120 of the sidewalls 114 and the anti-rotation surfaces 220 of the bolt 200 can be selected such that a component of a normal force provided by an anti-rotation surface 120 in a transverse, inward direction (e.g., toward a center of the opening 112) is sufficient to oppose rotation of the head 210 of the bolt when an anti-rotation surface 220 is in contact therewith, while a perpendicularly directed component of the normal force that is parallel to the longitudinal axis 222 of the bolt 200 can be sufficient to provide a secure contact between the anti-rotation surfaces 120, 220. In various embodiments, the angle α can be within a range of from about 30 degrees to about 75 degrees, from about 45 degrees to about 75 degrees, or from about 45 degrees to about 60 degrees; can be no more than about 45, 60, or 75 degrees; or can be no less than about 45, 60, or 75 degrees.

As previously mentioned, the anti-rotation surfaces 120, 220 can be substantially complementary to each other such that they contact one another along a substantial portion thereof. For example, in some embodiments, an entirety of an anti-rotation surface 220 of the bolt 200 can contact a corresponding anti-rotation surface 120 of the bone plate 100. In other embodiments, a smaller contact area may exist between the anti-rotation surfaces 120, 220. For example, in some embodiments, the bolt 200 can be used with the bone plate 100' shown in FIGS. 6A and 6B. The anti-rotation surfaces 220 thus may contact only an upper and lower line along a longitudinal length of each of the anti-rotation surfaces 120'. In other embodiments, the anti-rotation surfaces 220 of the bolt 200 may be substantially parabolic so as to be complementary to the anti-rotation surfaces 120' and thus contact a greater portion, or the entirety, thereof. Other complementary arrangements for the anti-rotation surfaces 120 or 120' and the anti-rotation surfaces 200 are contemplated. In various embodiments, the anti-rotation surfaces 120, 120', 220 can include friction-enhancing features. For example, the surfaces 120, 120', 220 can be roughened.

In some embodiments, only a portion of an anti-rotation surface 220 of the bolt 200 may contact a corresponding anti-rotation surface 120. For example, as previously discussed, the openings 112 of the bone plate 100 may be elongated such that the head 210 of the bolt 200 can translate longitudinally therein, up until the bolt 200 has been tightened down against the bone plate 100. Or stated otherwise, the elongated openings 112 can permit the head 210 of the bolt 200 to seat within the bone plate 100 within a range of acceptable longitudinal positions along the opening 112, which can aid in an indirect placement of the bolt 200 within a patient and/or can allow for a range of suitable drilled pathways through pelvic bones (e.g., can permit for less precise drilling through a bone), as will be further appreciated from the implantation methods discussed below. The bolt 200 thus can be received within an opening 200 at any of the acceptable orientations, and the portions of the anti-rotation surfaces 120, 220 that contact each other can assist in preventing rotation of the bolt 200 as it is tightened into place.

As shown in FIG. 8, the bolt 200 can define a conduit or lumen 230 that extends through the head 210 and the shaft 212. The lumen 230 can be divided into a proximal lumen 232 and a distal lumen 234. An outer periphery of the proximal lumen 232 can be defined by a substantially smooth inner sidewall 240, whereas an outer periphery of the distal lumen 234 can be defined by internal threading 242. Accordingly, an inner diameter of the proximal lumen 232 can be greater than an inner diameter of the distal lumen 234. In various embodiments, the internal threading 242 can cover different amounts of an internal surface of the bolt 200. For example, in some embodiments, the internal threading 242 can cover substantially an entire internal surface of the bolt 200. The internal threading 242 can be complementary to external threading of a screw (see FIG. 25). A screw thus can be advanced into the bolt 200 through a lower end 252 of the bolt 200.

Figure 9:
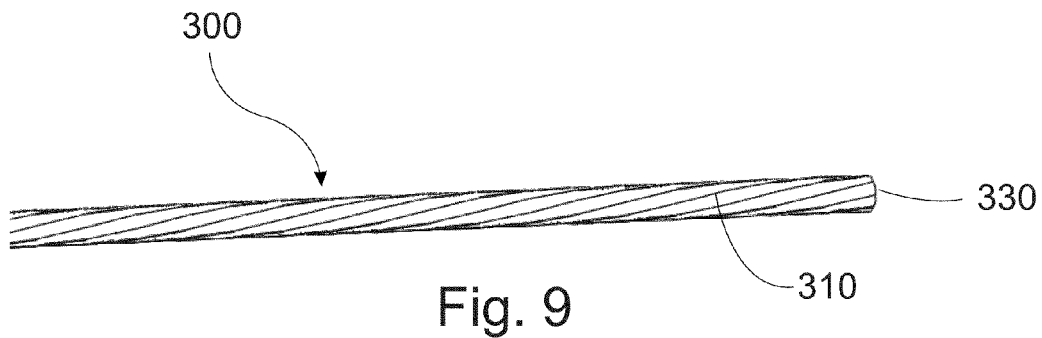
FIG. 9 is a perspective view of an embodiment of a cable.

FIG. 9 illustrates an embodiment of a cable 300 that can be used to position the bolt 200 through an opening of the bone plate 100 and into a hole in a pelvic bone, as described further below. The cable 300 can comprise any suitable material, such as, for example, stainless steel. In some embodiments, the cable 300 can desirably be radio opaque. The cable 300 can include multiple wires or strands 310 that are braided. The cable 300 can be substantially inextensible, such that a longitudinal length thereof is substantially constant, even when stressed. The cable 300 can be flexible, such that it can be readily bent or curved relative to a longitudinal dimension thereof. In certain embodiments, having multiple strands 310 of stainless steel that have relatively small diameters and which are braided together can contribute to the substantially inextensible yet flexible properties of the cable 300. The cable 300 can have any suitable length and diameter. In some embodiments, a length of the cable 300 is about 60 centimeters and a diameter of the cable 300 is about 1.4 millimeters.

In FIG. 9, a lateral end 330 of the cable 300 is shown in a frayed or separated state to better show the multiple braided strands 310. In practice, both the lateral end 330 and a medial end 320 (see FIG. 23) of the cable 300 can be capped, tightly wound, or otherwise come to a fine tip or rounded end such that the ends may be readily inserted into devices, such as the bolt 200.

Figure 10:
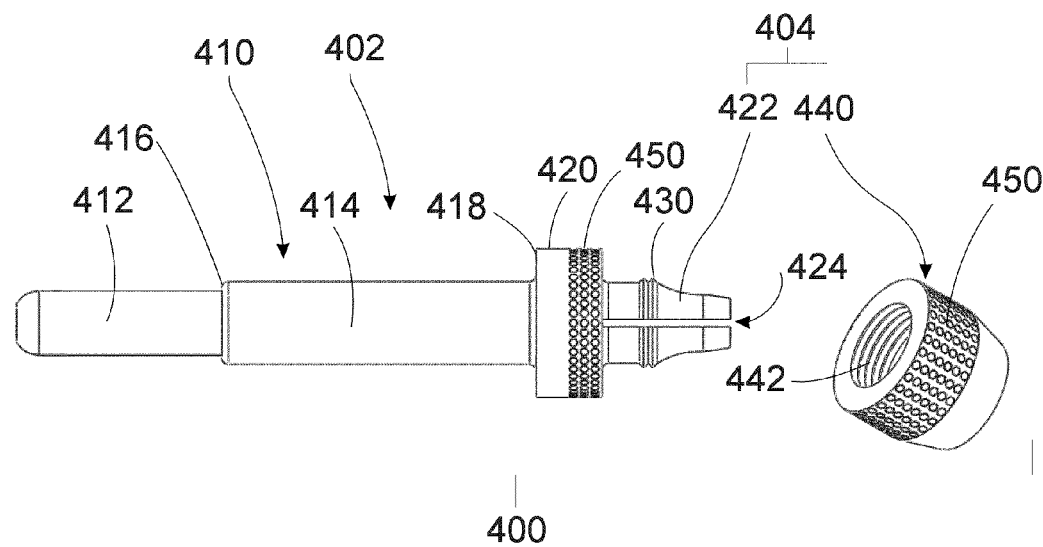
FIG. 10 is a perspective view of an embodiment of an orientation assembly in a disassembled state.

FIG. 10 illustrates an embodiment of a bolt orientation system 400 that can be selectively coupled to the cable 300 and used to position the bolt 200 through an opening of the bone plate 100 and into a hole in a pelvic bone, as described further below. The bolt orientation system 400 can comprise a plunger 402 that includes a clamping system 404.

The plunger 402 can include a tip or a tiered insert 410, which can be configured to be inserted into the lumen 230 of the bolt 200. For example, in the illustrated embodiment, the insert 410 includes a distal segment 412 and an intermediate segment 414. The distal segment 412 has a smaller outer diameter than does the intermediate segment 414. The distal segment 412 can transition to the intermediate segment 414 at a projection or rim 416 that projects radially outwardly from the distal segment 412 about a full periphery of the insert 410. Another projection or rim 418 can extend radially outwardly from a proximal end of the intermediate segment 414 about a full periphery of the insert 410, and can transition to a radially enlarged gripping segment 420. The plunger 402 can include a plurality of prongs 422 that extend proximally from the gripping segment 420.

The plunger 402 can define a lumen 424 through which the cable 300 can pass. The lumen 424 can extend through a full longitudinal length of the plunger 402 (e.g., through the prongs 422, the gripping segment 420, the intermediate segment 414, and the distal segment 412).

Figure 11:
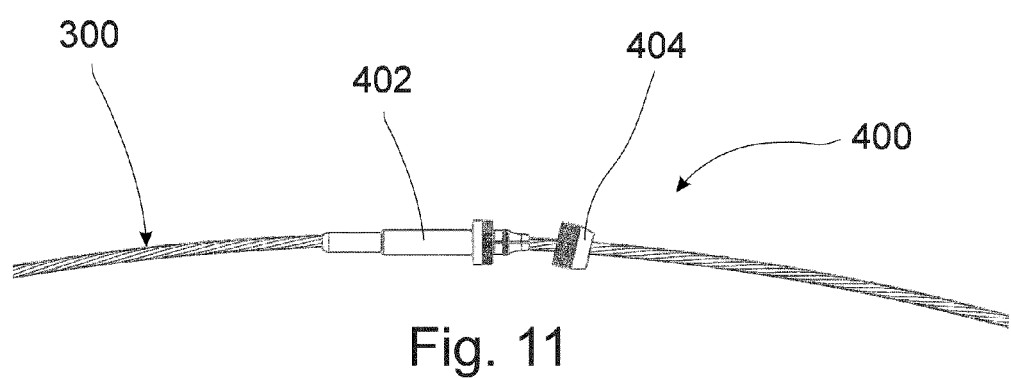
FIG. 11 is a perspective view of the orientation assembly of FIG. 10 positioned over an embodiment of a cable, wherein the orientation assembly is a translational state.

In the illustrated embodiment, the clamping system 404 includes the prongs 422, which have threading 430 at an exterior thereof, and a collar or cap 440, which has threading 442 at an interior thereof. Tightening the cap 440 onto the prongs 422 can deflect the prongs 422 inward so as to reduce the size of the portion of the lumen 424 that extends through the prongs 422. Accordingly, when the plunger 402 is positioned over the cable 300, as shown in FIG. 11, the cap 440 can be selectively tightened so as to fix the bolt orientation system 400 relative to the cable 300. Stated otherwise, the clamping system 404 can be configured to transition between a translational state and a clamping state. The clamping system 404 can be in the translational state when the cap 440 is removed from, or is relatively loosely connected to, the prongs 422 such that the plunger 402 is permitted to translate freely over the cable 300. The clamping system 404 can be in the clamping state when the cap 440 has been tightened onto the prongs 422 such that the prongs 422 deflect inwardly and grip the cable 300 so as to fix the plunger 402 relative to the cable 300. The gripping segment 420 and the cap 440 each can include a separate friction-enhancing surface 450 to aid in transitioning the clamping system 404 between the translational and clamping states. Other suitable selective clamping systems 404 also may be used with the cable 300.

As discussed further below, the plunger 402 can be configured to aid in positioning the bolt 200 within a hole that has been drilled in a pelvic bone. In some embodiments, the distal segment 412 of the insert 410 is sized to be received within the distal lumen 234 of the bolt 200, and the intermediate segment 414 of the insert 410 is sized to be received within the proximal lumen 232 of the bolt 200. In further embodiments, the distal segment 412 can frictionally engage the threads 242 that define an inner diameter of the distal lumen 234, and/or the intermediate segment 414 can frictionally engage the sidewall 240 that defines the proximal lumen 232. In other or further embodiments, when the plunger 402 is moved in a distal direction relative to the bolt 200, the rim 416 can contact a proximal surface of the threads 242 so as to urge the bolt 200 to move in the distal direction. In other or further embodiments, when the plunger 402 is moved in a distal direction relative to the bolt 200, the rim 418 can contact the proximal face 250 of the bolt 200 so as to urge the bolt 200 to move in the distal direction.

Engagement of the plunger 402 with the bolt 200 (see FIGS. 8 and 10) can provide sufficient force to the bolt 200 to cause it to move distally into a hole that has been drilled into a bone of the pelvis 10. In some embodiments, the engagement is frictional (e.g., engagement between the outer surface of the insert 410 and the threads 242 or sidewall 240), and in other or further embodiments, the engagement is abutting (e.g., engagement between the rim 416 and the threads 242 and/or engagement between the rim 218 and the proximal face 250). Once the bolt 200 has been inserted into the hole such that the bone frictionally engages an outer surface of the bolt 200, the engagement between the plunger 402 and the bolt 200 can be terminated by moving the plunger 402 in the proximal direction. For example, if the plunger 402 frictionally engages the bolt 200, the force of frictional engagement between the plunger 402 and the bolt 200 may be less than the force of frictional engagement between the bone and the bolt 200 such that the plunger 402 can be removed from the bolt 200 while the bolt 200 remains in position within the bone.

Figure 12A:
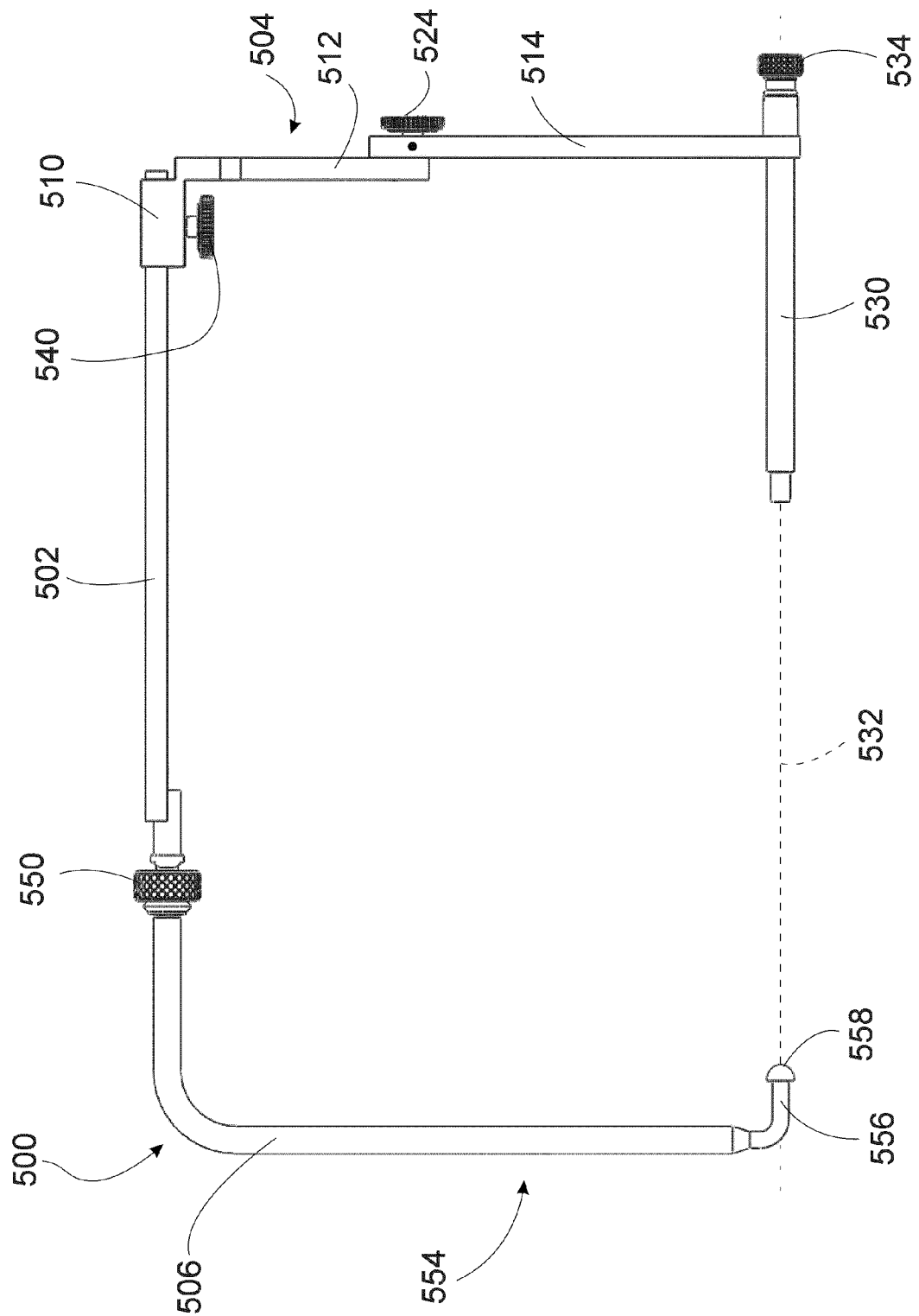
FIG. 12A is a perspective view of an embodiment of an alignment assembly.
Figure 12B:
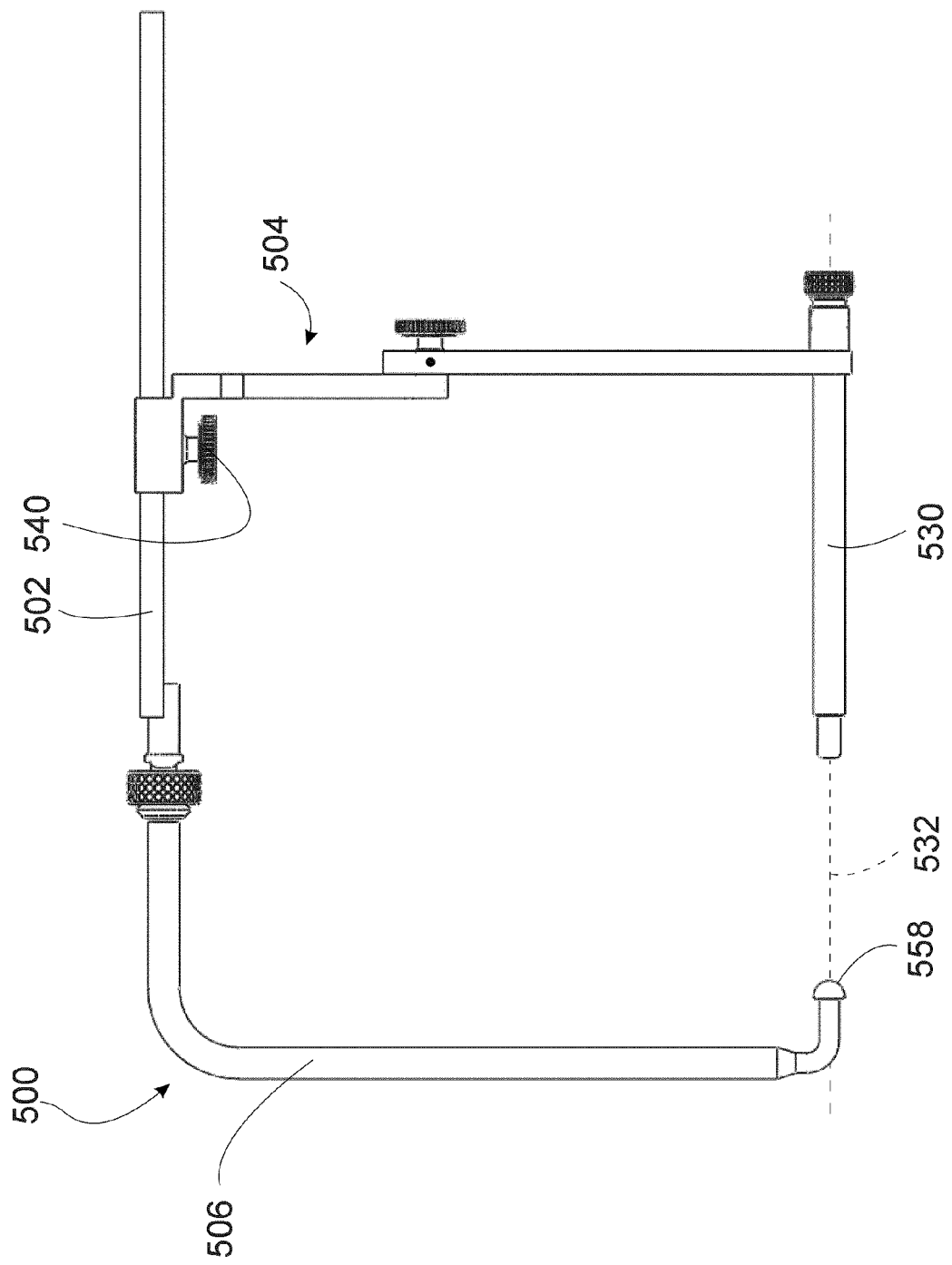
FIG. 12B is a perspective view of the alignment assembly of FIG. 12A in a different orientation in which an embodiment of a translational assembly has been approximated toward an embodiment of an alignment arm.
Figure 13:
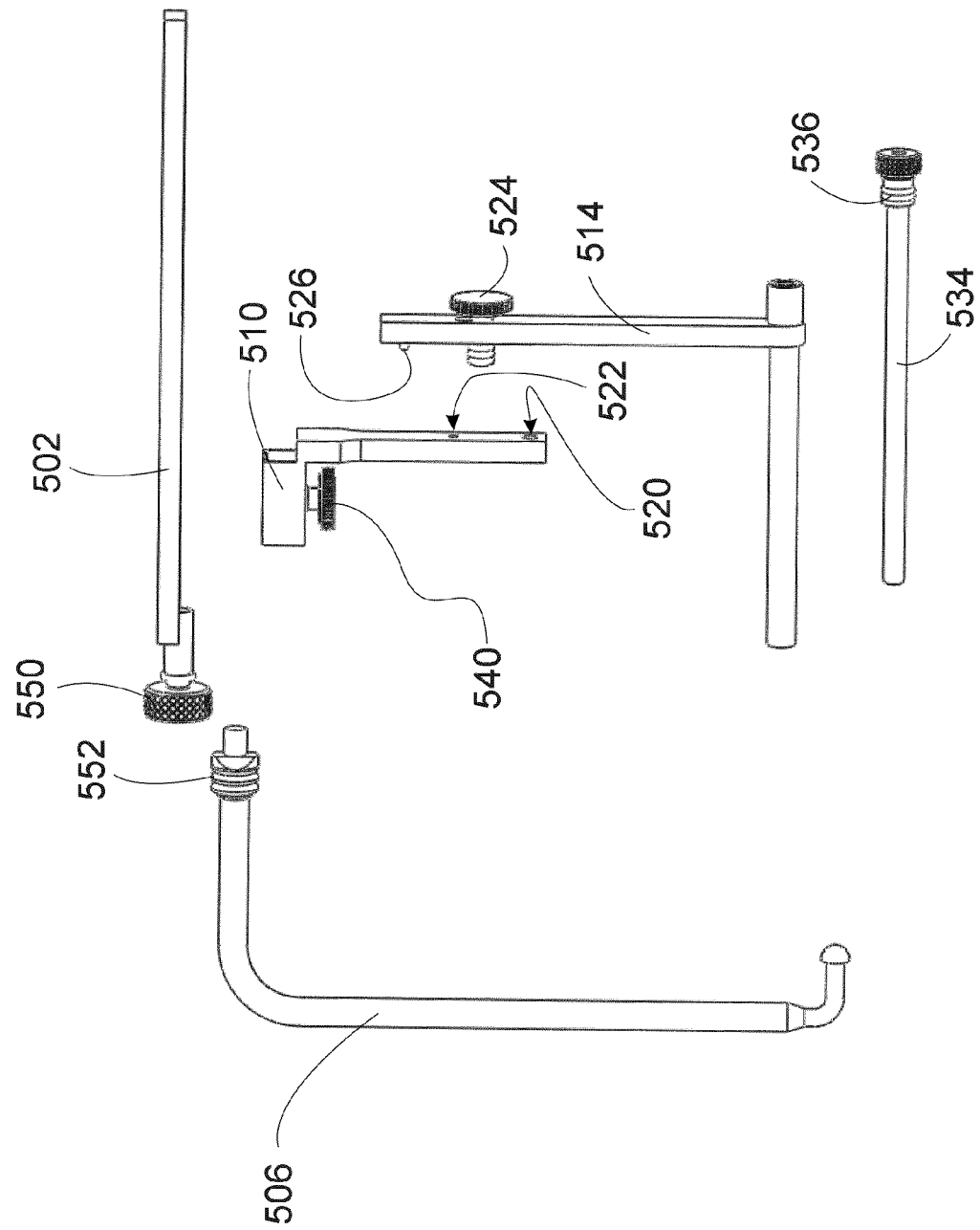
FIG. 13 is an exploded perspective view of the alignment assembly of FIG. 12A shown in a disassembled state.

FIGS. 12A, 12B and 13 illustrate an embodiment of an alignment assembly 500 that can be used in reverse implantation procedures, as discussed further below. In particular, the alignment assembly 500 can be used in positioning a guidewire and/or in drilling a hole or channel through a pelvic bone. The alignment assembly 500 can include a guiding arm 502, a translational assembly 504, and an alignment arm 506.

The translational assembly 504 can be selectively moveable relative to the guiding arm 502, and the alignment arm 506 can be fixed relative to the guiding arm 502.

The guiding arm 502 can be elongated along a longitudinal direction, and may be substantially linear such that the translational assembly 504 is configured to move along a linear path when translating relative to the guiding arm 504. In the illustrated embodiment, the guiding arm 502 defines a substantially rectangular outer perimeter along the longitudinal length thereof.

The translational assembly 504 can include a translational sheath 510 that cooperates with the guiding arm 504 to constrain movement of the translational assembly 504 to linear translation relative to the guiding arm 504, or stated otherwise, the translational sheath 510 can cooperate with the guiding arm 504 to permit movement of the translational assembly 504 relative to the guiding arm 504 without rotating relative to the guiding arm 504. For example, in the illustrated embodiment, the translational sheath 510 can define a substantially rectangular inner perimeter that is complementary to and can slide over the outer perimeter of the guiding arm 504. Other suitable arrangements for achieving translational and non-rotational motions between the translational assembly 504 and the guiding arm 502 are possible. For example, complementarities other than rectangular inner and outer perimeters may be used.

The translational assembly 504 can further include an attachment arm 512 and a translational arm 514. The attachment arm 512 can be fixedly attached to the translational sheath 510, and the translational arm 514 can be coupled to the attachment arm 512. In the illustrated embodiment, the translational arm 514 is coupled to the attachment arm 512 in a selectively removable manner. As shown in FIG. 13, the attachment arm 512 can include a threaded slot 520 and an opening 522. The translational arm 514 includes a threaded fastener 524 that can be selectively coupled to the threaded slot 520, and further includes a protrusion 526 that is received within the opening 522 to prevent rotational motion of the translational arm 514 relative to the attachment arm 512. Other arrangements for selectively fixing the translational arm 514 to the attachment arm 512 are also possible. For example, in some embodiments, the translational arm 514 can include one or more of the slot 520 and the opening 522, while the attachment arm 514 can correspondingly include one or more of the fastener 524 and the protrusion 526.

An elongated protection sleeve 530 can be attached to the translational arm 514. In the illustrated embodiment, the protection sleeve 530 is substantially cylindrical and defines a central axis 532. The central axis 532 can be substantially perpendicular to the translational arm 514 and substantially parallel to the guiding arm 502. The protection sleeve 530 can define a lumen through which a drill bit can be inserted, as further discussed below.

A constriction sleeve 534 can be inserted into the lumen of the protection sleeve 530 and may be selectively coupled to the protection sleeve 530. For example, in the illustrated embodiment, an outer surface of the constriction sleeve 534 comprises threading 536 that can cooperate with threading (not shown) at an internal surface of the protection sleeve 530. When it is received within the protection sleeve 530, the constriction sleeve 534 can be substantially coaxial with the protection sleeve 530 such that a central axis defined by the constriction sleeve 534 is aligned with the central axis 532 of the protection sleeve 530. The constriction sleeve 534 can define a lumen having a smaller transverse dimension (e.g., inner diameter) than a similar transverse dimension defined by the lumen of the protection sleeve 530. As further discussed below, a guidwire can be inserted through the lumen of the constriction sleeve 534.

The alignment assembly 500 can include an actuator 540 that is configured to selectively permit movement of the translational assembly 504 relative to the guiding arm 502. In particular, the actuator 540 can be transitioned between an unfixed orientation and a fixed orientation. When the actuator 540 is in the unfixed orientation, the translational assembly 504 can move along the guiding arm 502, whereas when the actuator 540 is in the fixed orientation, the translational assembly 504 can be prevented from moving relative to the guiding arm 502. In the illustrated embodiment, the actuator 540 comprises a rotatable fastener 542 that can selectively clamp against the guiding arm 502 or selectively disengage from the guiding arm 502.

In some embodiments, the alignment assembly 500 is configured for two-handed operation. For example, in the illustrated embodiment, the guiding arm 502 or the alignment arm 506 can be held in a first hand of a practitioner, and the translational assembly 504 can be operated with a second hand of the practitioner. The actuator 540 is positioned sufficiently closely to the attachment arm 512 that the practitioner can hold the attachment arm 512 with some portion of the hand while manipulating the actuator 540 with another portion of the hand (e.g., with the thumb and pointer finger). In other embodiments, the practitioner may manipulate the actuator 540 without holding onto the attachment arm 512 or the translational arm 514. For example, the actuator 540 may be spaced from the attachment arm 512 and the translational arm 514 such that the actuator 540 cannot be reached with a hand that is holding the attachment arm 512 and/or the translational arm 514.

Other arrangements for the actuator 540 are also contemplated. For example, in some embodiments, the actuator 540 comprises a lever that can be transitioned between the fixed and unfixed orientations. In some embodiments, the actuator 540 can comprise a squeezable handle similar to that of a caulking gun. The actuator 540 can be sequentially transitioned between the unfixed and fixed orientations to incrementally advance the translational arm toward the alignment arm 506 in a manner similar to the movement of a plunger of a caulking gun. In still other embodiments, the actuator 540 can comprise a pawl and the guiding arm 502 can comprise a line of teeth that interact with the pawl to permit movement of the translational assembly 540 naturally in only a single direction (e.g., toward the alignment arm 504). In certain of such embodiments, the actuator 540 can comprise a lever for disengaging the pawl from the teeth so as to permit movement of the translational assembly 540 in an opposite direction (e.g., away from the alignment arm 504).

The alignment arm 506 can be fixed relative to the guiding arm 502. In the illustrated embodiment, the alignment arm 506 is selectively removable from the guiding arm 504. As shown in FIG. 13, the guiding arm 504 includes a threaded collar 550 which can be selectively secured to a threaded end 552 of the alignment arm 506. The alignment arm 506 can include a transverse portion 554 that extends in a direction that is substantially perpendicular to the linear guiding arm 502. The transverse portion 554 of the alignment arm 506 can be substantially parallel to the attachment arm 512 and the translational arm 514. A distal end of the alignment arm 506 can include an extension segment 556 and an alignment tip 558. The extension segment 556 can be aligned with the central axis 532 defined by the protection sleeve 530. The alignment tip 558 can be configured to fit snugly within an opening 112 of the bone plate 100. For example, the alignment tip 558 can be substantially ball-shaped or chamferred. An outer surface of the alignment tip 558 can be complementary to a cross-sectional contour of the sidewall 114 of the openings 112 of the bone plate 100.

With reference to FIGS. 12A and 12B, movement of the translational assembly 504 is demonstrated. When the translational assembly 504 is in the position shown in FIG. 12A, the actuator 540 can be moved to the unfixed orientation, thereby permitting the translational assembly 504 to translate relative to the guiding arm 502. As shown in FIG. 12B, as the translational assembly 504 is moved toward the alignment tip 558, the protection sleeve 530 can remain aligned with the alignment tip 558. Stated otherwise, the central axis 532 defined by the protection sleeve 530 can maintain a substantially fixed orientation relative to the guiding arm 502 such that the central axis 532 extends through the alignment tip 558 as the translational assembly 504 is advanced toward the alignment arm 506. In practice, a distal end of the protection sleeve 530 can come into contact with an outer surface of a pelvic bone and can be stopped thereby when the alignment tip 558 is seated in an opening of a bone plate 100 that is being implanted in a patient.

Figure 14:
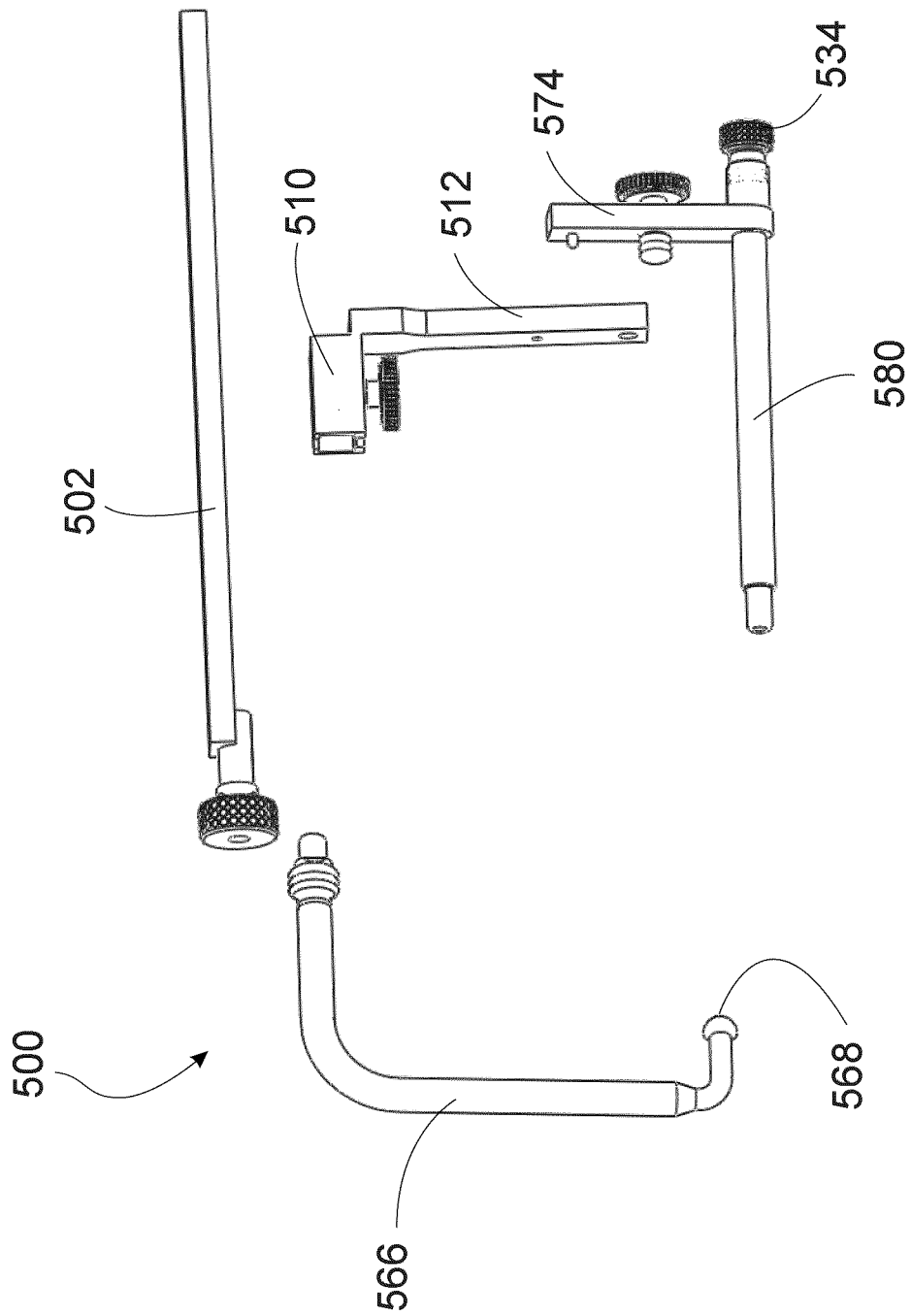
FIG. 14 is an exploded perspective view of the alignment assembly of FIG. 12A in which the longer alignment arm and a longer translational arm components shown in FIGS. 12A, 12B, and 13 have been replaced with a shorter alignment arm and a shorter translational arm.

With reference to FIGS. 13 and 14, in some embodiments, the alignment assembly 500 is adjustable such that it can be used to form holes through a pelvic bone that are at more shallow or more greater depths relative to an incision site. In the illustrated embodiment, the alignment arm 506 and the translational arm 514 (FIG. 13) are relatively long and can be used for drilling holes that are relatively distant from a primary incision site. A second alignment arm 566 and a second translational arm 574 (FIG. 14) can be interchangeable with the alignment arm 506 and the translational arm 514, respectively, and can be used for drilling holes that are at more shallow depths. Stated otherwise, the alignment arm 566 and the translational arm 574 are shorter than the alignment arm 506 and the translational arm 514. In other or further embodiments, one or more additional sets of translational arms and alignment arms may be used for different depths.

Other than defining shorter lengths, the alignment arm 566 and the translational arm 574 can closely resemble the alignment arm 506 and the translational arm 514, respectively. For example, the alignment arm 566 can include an alignment tip 568, and the translational arm 574 can include a protection sleeve 580 that can be selectively coupled with the constriction sleeve 534. The protection sleeve 580 can define a central axis 582 that is aligned with the alignment tip 568 when the alignment assembly 500 is assembled using the alignment arm 566 and the translational arm 574 (i.e., when the translation sleeve 510 is positioned over the guiding arm 502 with the translational arm 574 connected to the attachment arm 512, and when the alignment arm 566 is attached to the guiding arm 502). In some embodiments, the shorter alignment arm 566 and translational arm 574 can be used during at least a portion of a procedure for implanting a bone plate 100 in a substantially horizontal orientation relative to the anterior and posterior columns. In some embodiments, the longer alignment arm 506 and translational arm 514 can be used during at least a portion of a procedure for implanting a bone plate 100 in a substantially vertical orientation along a posterior column.

The alignment assembly 500 can be formed of any suitable material. For example, in various embodiments, one or more portions of the alignment assembly 500 can comprise stainless steel. In some embodiments, the alignment assembly 500 or portions thereof can be disposable. In other or further embodiments, at least a portion of the alignment assembly 500 can be composed of durable materials that can readily be sterilized between multiple uses.

Illustrative methods by which a bone plate 100 can be implanted in a substantially vertical orientation, such as that shown in FIG. 1, are provided hereafter. The longer alignment arm 506 and translational arm 514 may be used with the alignment assembly 500 for certain stages of the methods. The methods are described in sufficient detail for those skilled in the art to understand their implementation, thus details that may be generally applicable to other surgical procedures may not be mentioned or described at length. Moreover, some steps, or portions thereof, are described with a relatively high degree of specificity. While inventive aspects may lie in the specifics thus described, it is to be understood that the specifics are not necessarily limiting, such that omissions thereof or alterations thereto are also possible.

In certain methods, various images of a patient 600 are obtained to determine the nature of a fractured acetabulum of the patient 600. The images may be obtained in any suitable manner. In some embodiments, the five standard X-ray projections for the pelvis and acetabulum are obtained, which projections include the anteriorposterior view, the inlet and the outlet of the pelvis, and the two oblique acetabular projections. It can be desirable for the alar and obturator view of one acetabulum to include the opposite view of the other acetabulum within the same film or frame. For example, where the alar view of the right acetabulum is obtained, the same film or frame would include an obturator view of the left acetabulum, and vice versa. Pelvis computer tomography can be performed to complement simple X-ray studies in order to better identify fracture fragments, displacements, and intrarticular fragments.

Based on the obtained images, drawings or other suitable representations of the fractured portion of the pelvis 10 can be prepared. In some cases, it can be desirable to prepare drawings of at least two projections, such as the anteriorposterior view combined with either an alar or obturator view, depending on the fracture pattern. The non-fractured side of the pelvis 10 can be used as template for the drawings. For example, a mirror image of the non-fractured side of the pelvis 10 can be rendered in a drawing, and fracture lines can be added to the drawing based on the images that were obtained of the fractured side of the pelvis. Based on the drawing, it can be determined whether the bone plate 100 should be fixed in a substantially horizontal or substantially vertical orientation in order to best span the fracture and reduce the fragments. As previously mentioned, the present discussion is directed to methods in which the bone plate 100 is implanted in a substantially vertical orientation relative to the posterior column. Methods in which a substantially horizontal orientation is desired are described below.

A schematic representation of the bone plate 100 can be added to the drawing of the fractured pelvis 10 to determine the desired orientation of the plate 100. The actual bone plate 100 can then be bent to the desired shape or contour based on the drawing. It can be desirable to use an artificial (e.g., plastic) pelvis as a template to obtain the desired contour of the bone plate 100. As previously mentioned, in various embodiments, the bone plate 100 can be bent by bare hand or with the aid of pliers or a bending press.

Figure 15:
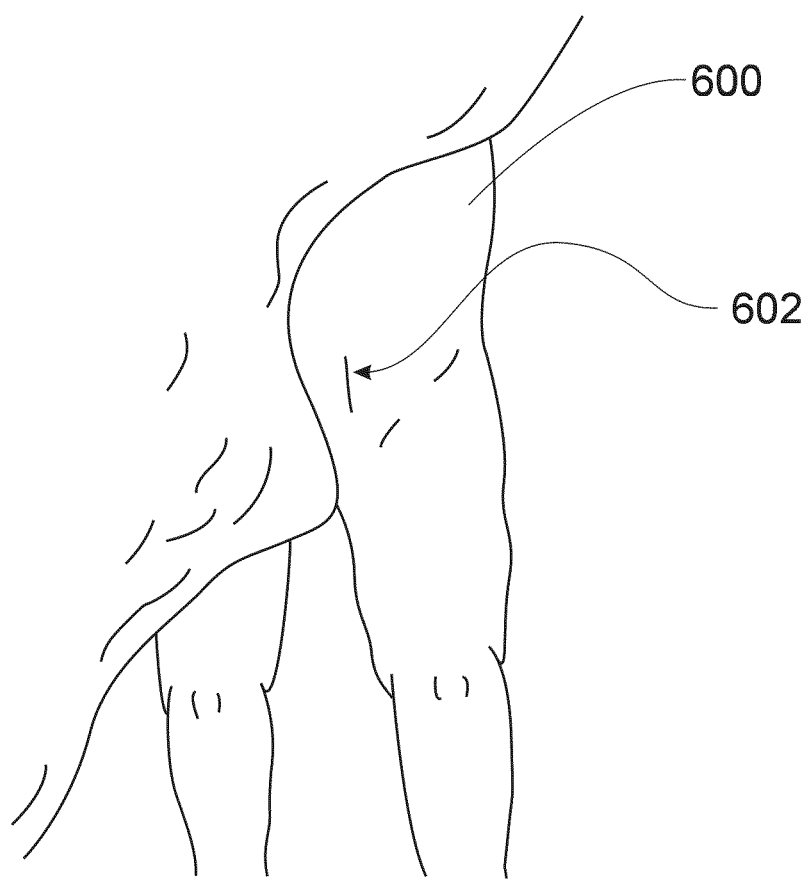
FIG. 15 is a front plan view of a minimally invasive primary incision that has been created in an abdominal region of a patient.

With reference to FIG. 15, the patient 600 is placed in a supine position with a sandbag (not shown) beneath the ipsilateral renal fossa. A vertical incision 602 is then made. In some methods, the incision 602 is initiated approximately 1 centimeter proximal to the inguinal line and is extended proximally a distance of from about 8 to about 10 centimeters to a position that is about 3 centimeters medial to the femoral vessels. Stated more generally, a primary incision 602 can be made in the abdominal region of the patient 600.

The abdominal muscles and fascia transversalis are sharp dissected vertically. The internous obturator muscle is digitally identified and is dissected via the surgeon's fingers. The quadrilateral wall, the iliopectineal line, and the fracture fragments (and the respective displacements thereof) are then digitally indentified. It can be desirable to digitally dissect the obturator muscle so as to be able to touch the quadrilateral wall and the fracture fragments. It is noted that in young patients, this muscle can be wide and strong. The contoured bone plate 100 is then inserted through the primary incision 602 and is presented over the fracture along the posterior acetabular column. During this step, attention can be taken to avoid trapping the obturator nerve and artery between the bone plate 100 and the pelvis 10. Proper positioning of the plate 100 within the true pelvis 30 can be verified by an image intensifier.

Figure 16:
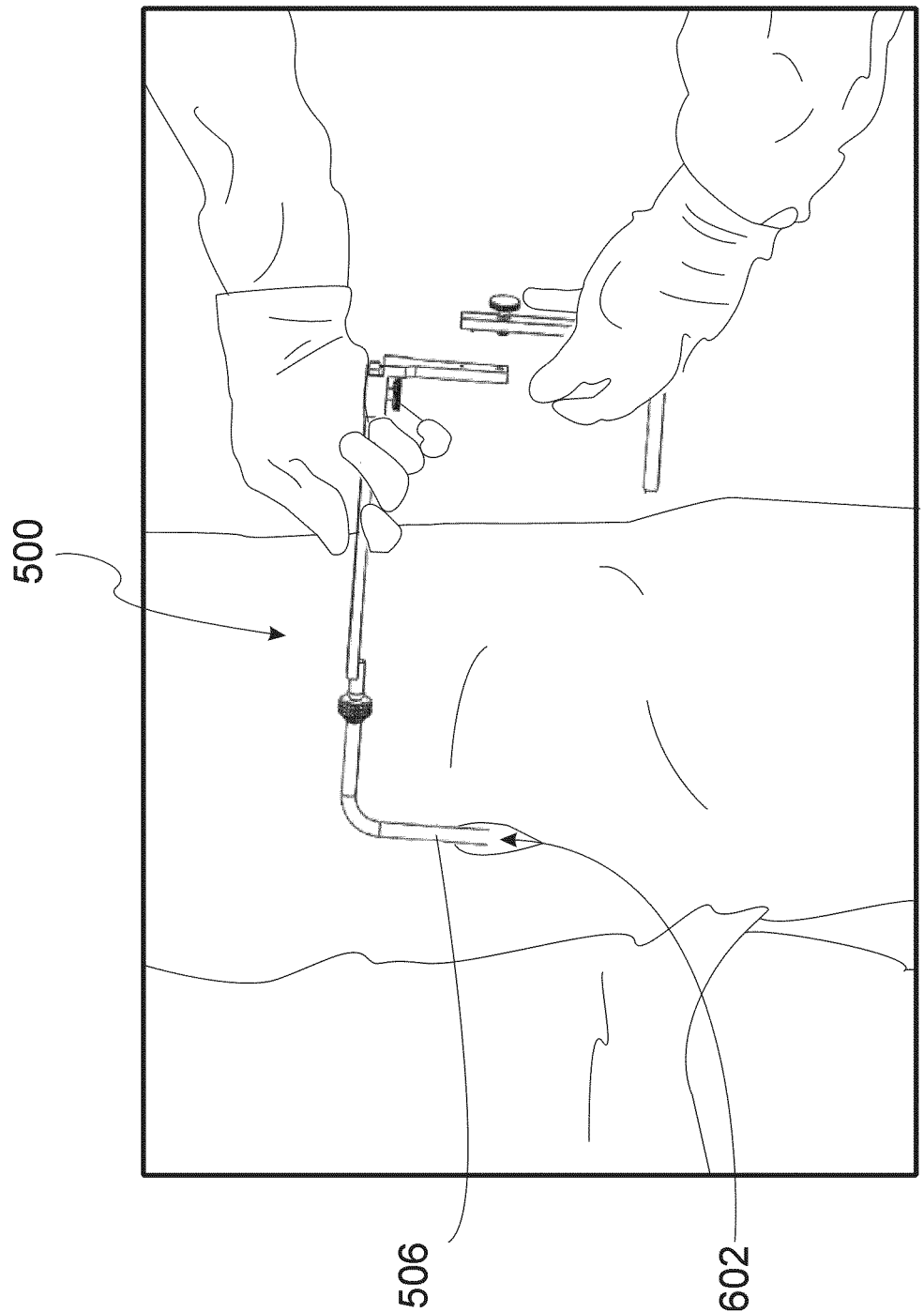
FIG. 16 is a perspective view showing the alignment arm of the alignment assembly of FIG. 12A having been inserted into the primary incision of FIG. 15.
Figure 17:
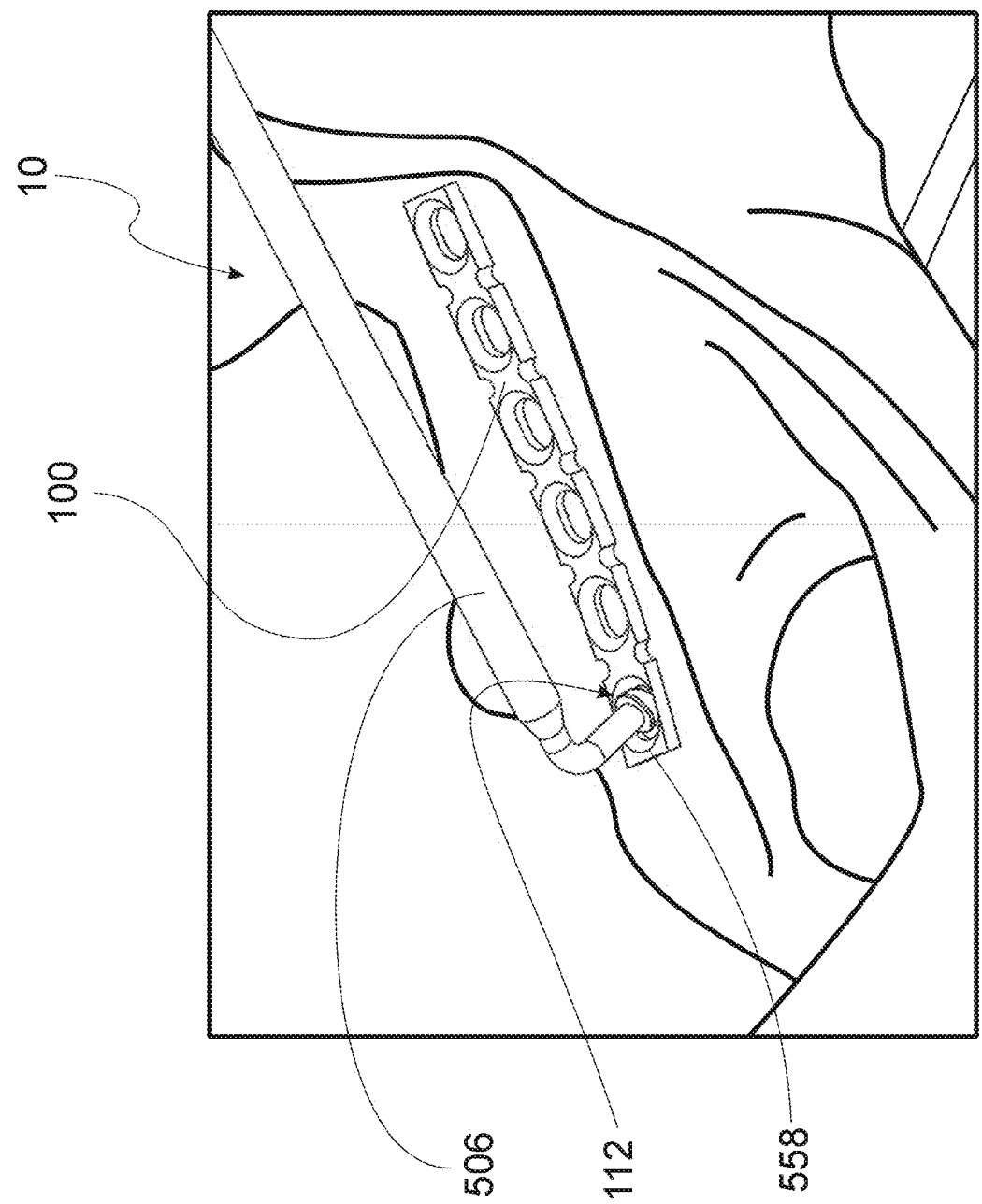
FIG. 17 is a perspective view of the alignment tip of the alignment assembly of FIG. 12A positioned in an opening of the bone plate of FIG. 2, which is positioned within the true pelvis of a patient.

With reference to FIG. 16, the alignment arm 506 of the alignment assembly 500 is introduced into the primary incision 602 and is advanced to a deeply located portion of the posterior column 32. As shown in FIG. 17, the alignment tip 558 can be placed in the desired opening 112 of the bone plate 100. In the illustrated embodiment, the alignment tip 558 is inserted into the opening 112 that is the second from the bottom of the bone plate 100 (i.e., the opening 112 that is adjacent to the most distal opening 112). It is noted that skin, tissue, and further anatomical features other than the pelvis 10 are not shown in FIG. 17 so as not to obscure the bone plate 100 and the alignment arm 506. In practice, the bone plate 100 and the alignment arm 506 would be more difficult to see (e.g., would not be fully visible from the perspective shown in FIG. 17), given the small size of the primary incision 602.

Figure 18:
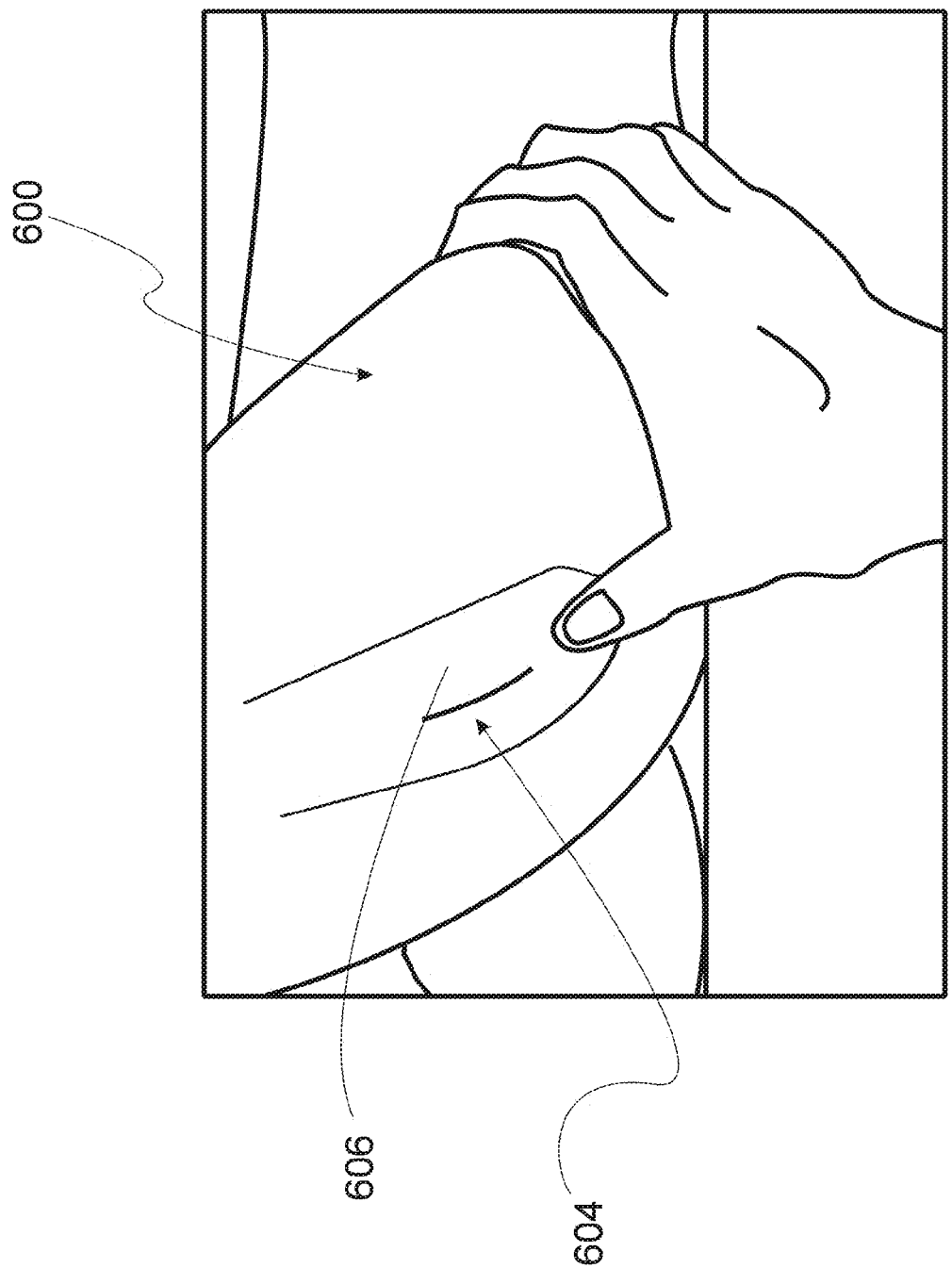
FIG. 18 is a perspective view of a secondary incision that is lateral to the primary incision, along with markings made to assist in creating the secondary incision.

With the bone plate 100 and the alignment tip 558 positioned as desired, a secondary incision 604 can be made at a position that is lateral to the first incision 602, as shown in FIG. 18. For example, the site of the secondary incision 604 can be determined by positioning the hip of the patient 600 at a 90 degree angle. A line 606 from the superior and anterior iliac spine to the center of the greater trochanter can be extended half of the distance between the anterior and superior iliac spine and the center of the greater trochanter. The ischium body can be localized by palpation, and the secondary incision 604 can be made at that point. Tissue can then be spread (e.g., via a Kelly clamp), with careful attention being paid not to disturb the sciatic nerve.

In some methods, the alignment assembly 500 can desirably be used in determining the desired location of the secondary incision 604. For example, once the alignment arm 506 is in place in the manner described above, the translational assembly 504 can be advanced toward the skin of the patient until a distal end of the protection sleeve 530 just touches the skin and makes an impression therein. The translational assembly 504 can then be retracted away from the skin. The impression left by the protection sleeve 530 can serve as a reference point for creation of the secondary incision 604, and can aid in ensuring that subsequent advancement of the protection sleeve 530 through the secondary incision 604 will yield a desired alignment of the protection sleeve 530 with the alignment tip 558.

Figure 19:
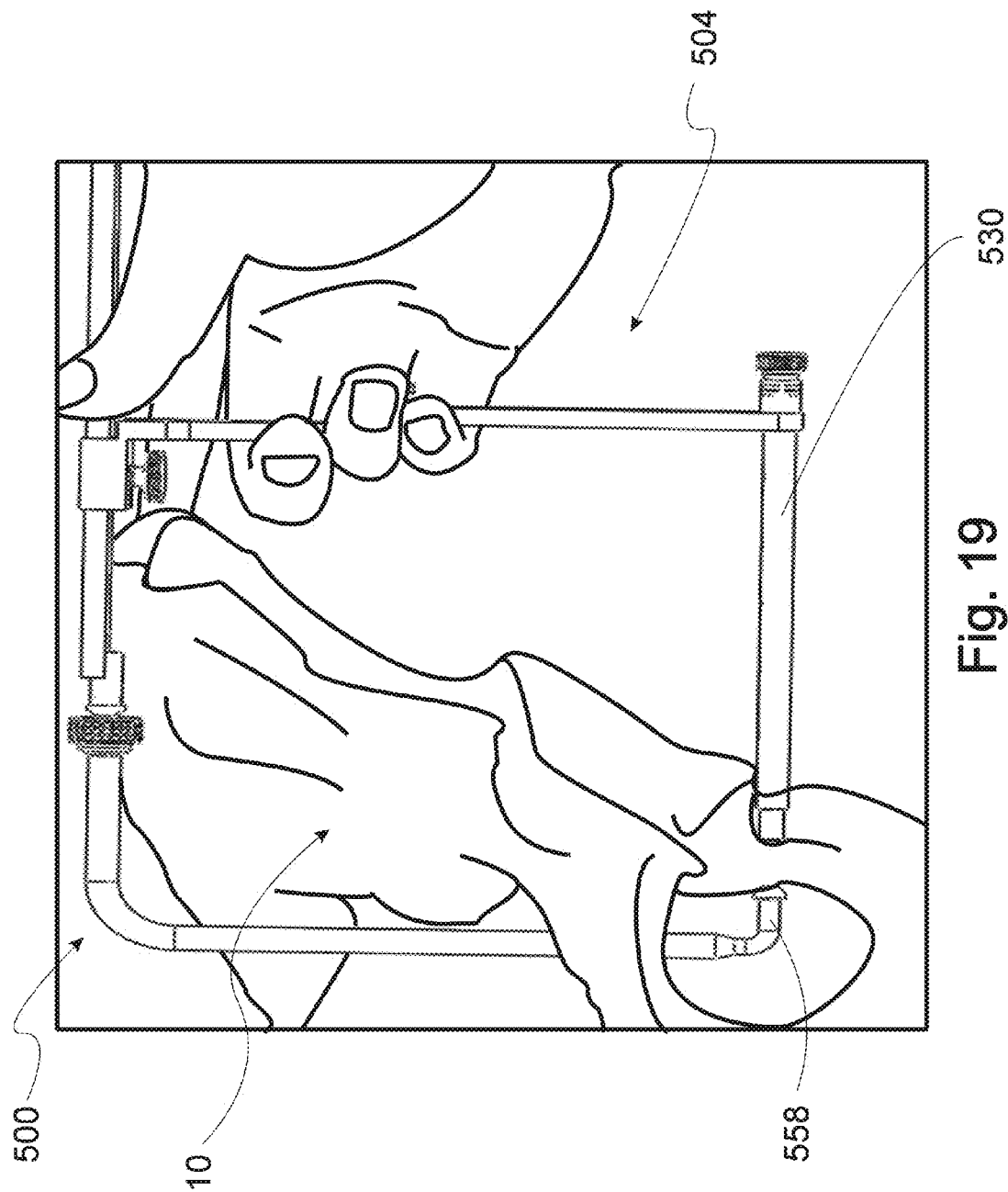
FIG. 19 is a perspective view of the alignment assembly of FIG. 12A in an orientation in which the alignment tip is within the opening of the bone plate, as shown in FIG. 17, and the protection sleeve has been moved into contact with an outer surface of the pelvis.

Once the secondary incision 604 has been created, the translational assembly 504 is advanced toward the alignment arm 506. In so doing, the protection sleeve 530 is introduced into the secondary incision 604 and is advanced very slowly until bone is felt. An image intensifier can be used to verify that the alignment assembly 500 is in the desired orientation with the alignment tip 558 in contact with (or in close proximity to) an interior surface of the pelvis 10 and the protection sleeve 530 in contact with an exterior surface of the pelvis 10, as shown in FIG. 19. As with FIG. 17, skin, tissue, and other anatomical features are not shown in FIG. 19 so as to more clearly illustrate the orientation of the alignment assembly 504 relative to the pelvis 10.

Figure 20:
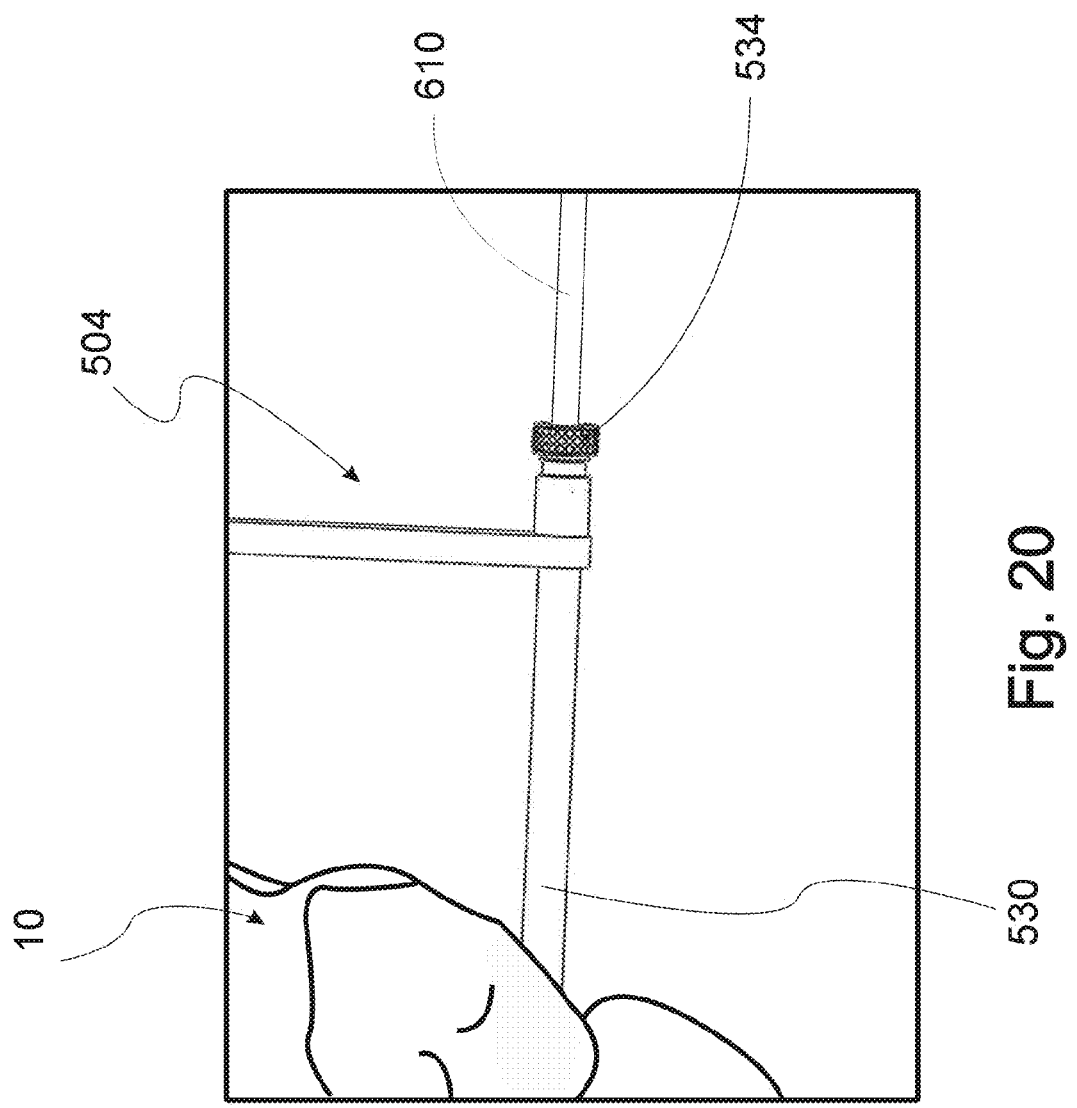
FIG. 20 is a perspective view of a portion of the alignment assembly with a guidwire being inserted through a constriction sleeve that is within the protection sleeve.

With reference to FIG. 20, once the desired positioning of the translational assembly 504 has been achieved, a guidewire or Kirschner wire ("K wire") 610 is introduced into the constriction sleeve 534 of the alignment assembly 500. As previously discussed, the constriction sleeve 534 can define lumen that is sized just larger than an outer diameter of the guidwire 610. In some embodiments, the outer diameter of the guidewire 610 is about 2.5 millimeters, although other sizes can be suitable. With a tight fit or close correlation between the lumen of the constriction sleeve 534 and the outer diameter of the guidewire 610, the guidewire 610 can be inserted into the bone along a path that is substantially aligned with the central axis 532 of the protection sleeve 530 and the alignment tip 558.

The guidewire 610 thus is advanced into the pelvic bone from the lateral side of the pelvis 10 (e.g., through an exterior surface of the pelvis 10) and is advanced toward or into the true pelvis 30 (e.g., toward or through an interior surface of the pelvis 10). Stated otherwise, the guidewire 610 is advanced into the pelvic bone in a lateral-to-medial direction.

Figure 21:
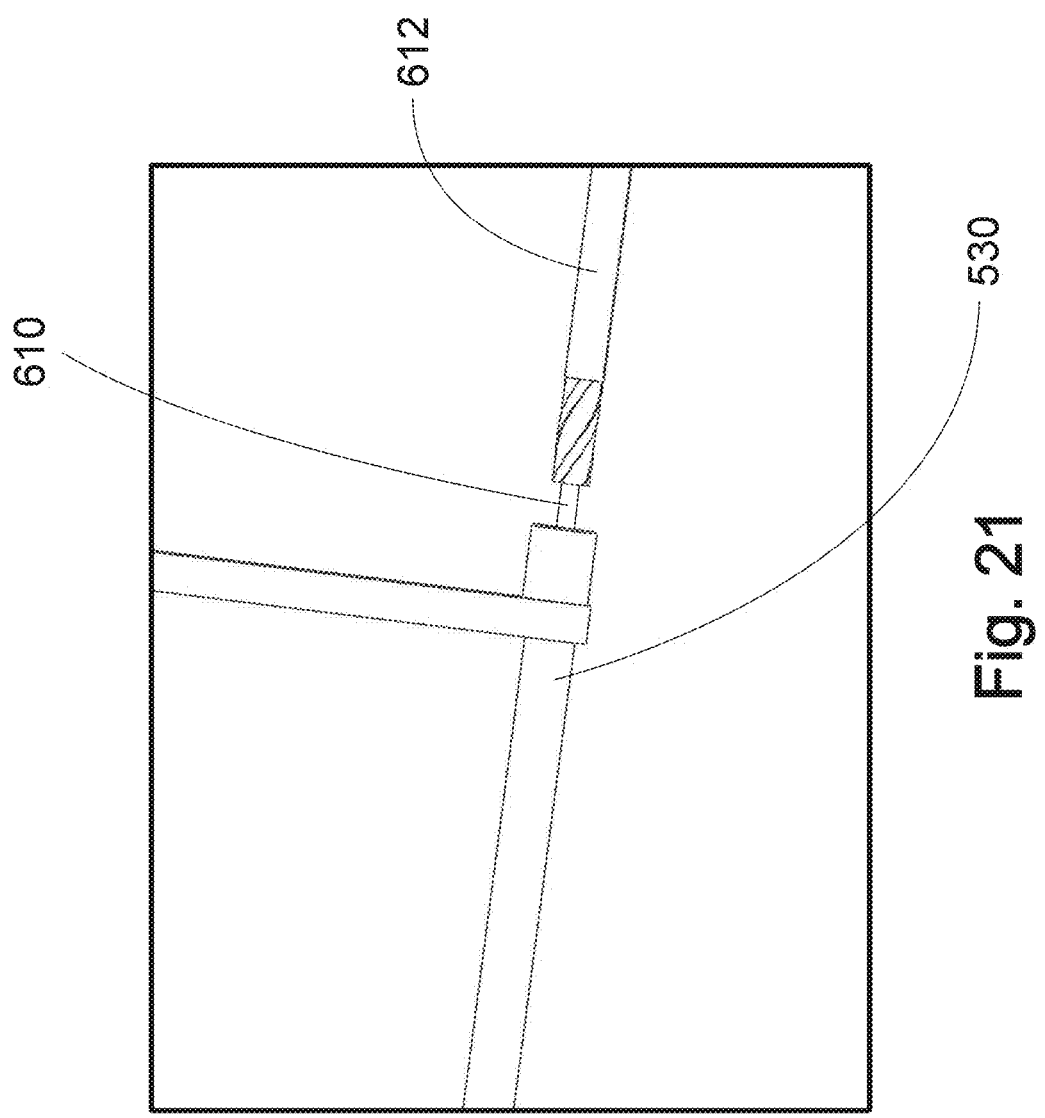
FIG. 21 is a perspective view of a portion of the alignment assembly with the constriction sleeve having been removed from the protection sleeve and with a cannulated drill be being inserted over the guidewire and into the protection sleeve.

As shown in FIG. 21, once the guidwire 610 has been positioned as desired, the constriction sleeve 534 is removed from the protection sleeve 530. A cannulated drill bit 612 (e.g., a 6.0 millimeter outer diameter bit) is then inserted over the guidewire 610 and into the lumen defined by the protection sleeve 530. A hole is then drilled in the pelvic bone in a lateral-to-medial direction. The hole can extend fully through the pelvic bone such that an open end thereof is at the opening 112 of the bone plate 100 at which the alignment tip 558 is situated.

Once the hole through the pelvic bone has been created as desired, the alignment assembly 500 can be removed from the patient 600. For example, in some embodiments, the guiding arm 502 is uncoupled from the alignment arm 506. The guiding arm 502 and the translational assembly 504 can then be moved in a lateral direction over the drill bit 612, whereas the alignment arm 506 can be removed from the primary incision 602 in a direction that is substantially perpendicular to the lateral direction in which the guiding arm 502 and translation assembly 504 were removed. In other embodiments, the guiding arm 502 can be uncoupled from the translational assembly 504, the translational assembly 504 can be removed in the lateral direction, and both the guiding arm 502 and alignment arm 506 can be removed in the substantially perpendicular direction while they remain coupled to each other. Other removal techniques are also possible.

Figure 22:
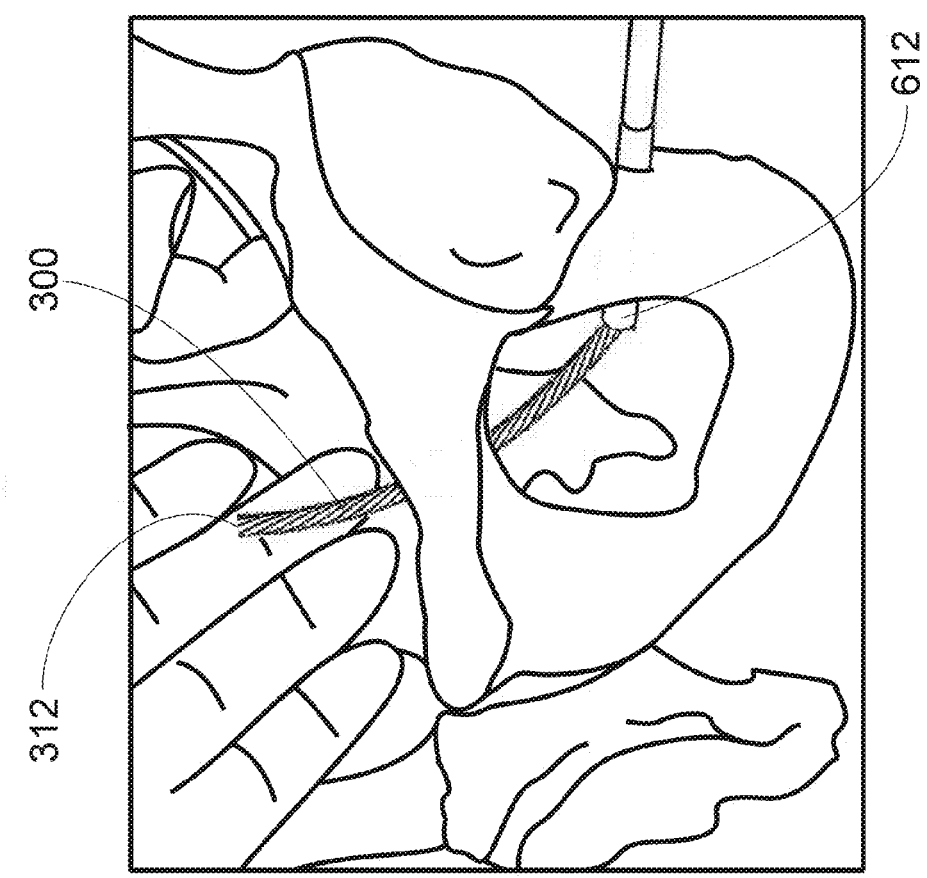
FIG. 22 is a perspective view of a practitioner guiding a medial end of the cable out of the true pelvis of the patient and through the primary incision (which is not shown in FIG. 22)

The drill bit 612 can remain within the hole through the pelvic bone that has been drilled. The guidewire 610 can be removed from the drill bit 612 in a medial-to-lateral direction. The cable 300 can then be inserted through the channel of the drill bit 612 in a lateral-to-medial direction. As shown in FIG. 22, a medial end 320 of the cable 300 can be fed into the true pelvis and then directed out of the patient 600 through the primary incision 602. The drill bit 612 is then gently removed from the patient 600 over the lateral tip 330 of the cable 300 so as to leave the cable 300 within the pelvic bone. Both the medial tip 320 and the lateral tip of the cable 300 can be positioned outside of the patient 600 such that the cable 300 extends laterally (e.g., out of a secondary incision 604) as well as ventrally (e.g., out of the primary incision 602).

Figure 23:
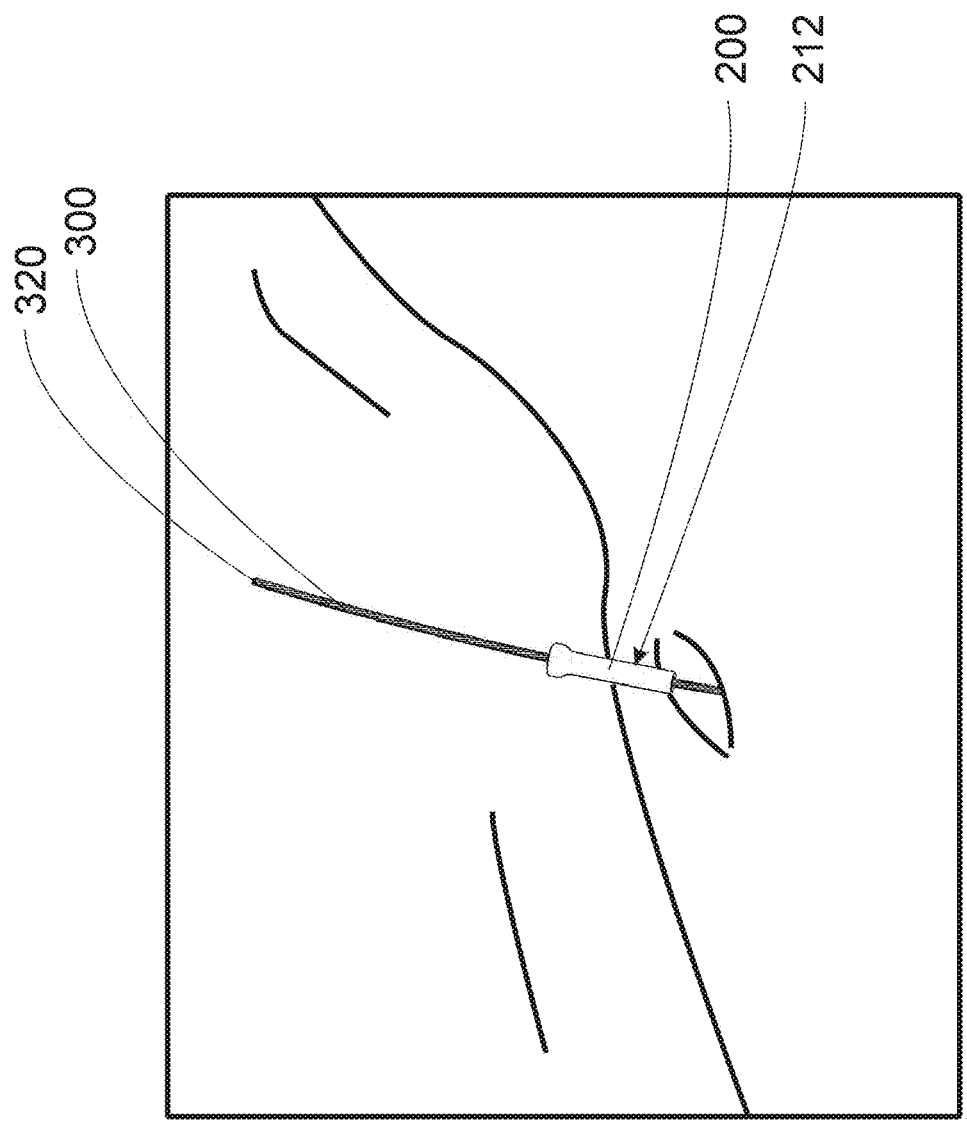
FIG. 23 is a perspective view of the bolt of FIG. 7 being advanced over the medial end of the cable.

As shown in FIG. 23, the bolt 200 can be advanced over the cable 300, shaft 212 first. The orientation system 400 can then be advanced over the cable 300, and the insert 410 can be inserted into the bolt 200 in a manner such as discussed above with respect to FIGS. 8 and 11. Either before or after situating the insert 410 within the bolt 200, the clamping system 404 of the orientation system 400 can be transitioned to the clamping state so as to fix the clamping system 404 relative to the cable 300. In some embodiments, the orientation system 400 is attached to the cable 300 at a position about 10 centimeters from the medial end 320 of the cable 300. Once the orientation system 400 is secured to the cable 300 and the bolt 200 is positioned thereon, the cable 300 can be carefully advanced in the medial-to-lateral direction so as to advance the bolt 200 through the primary incision 602.

Figure 24:
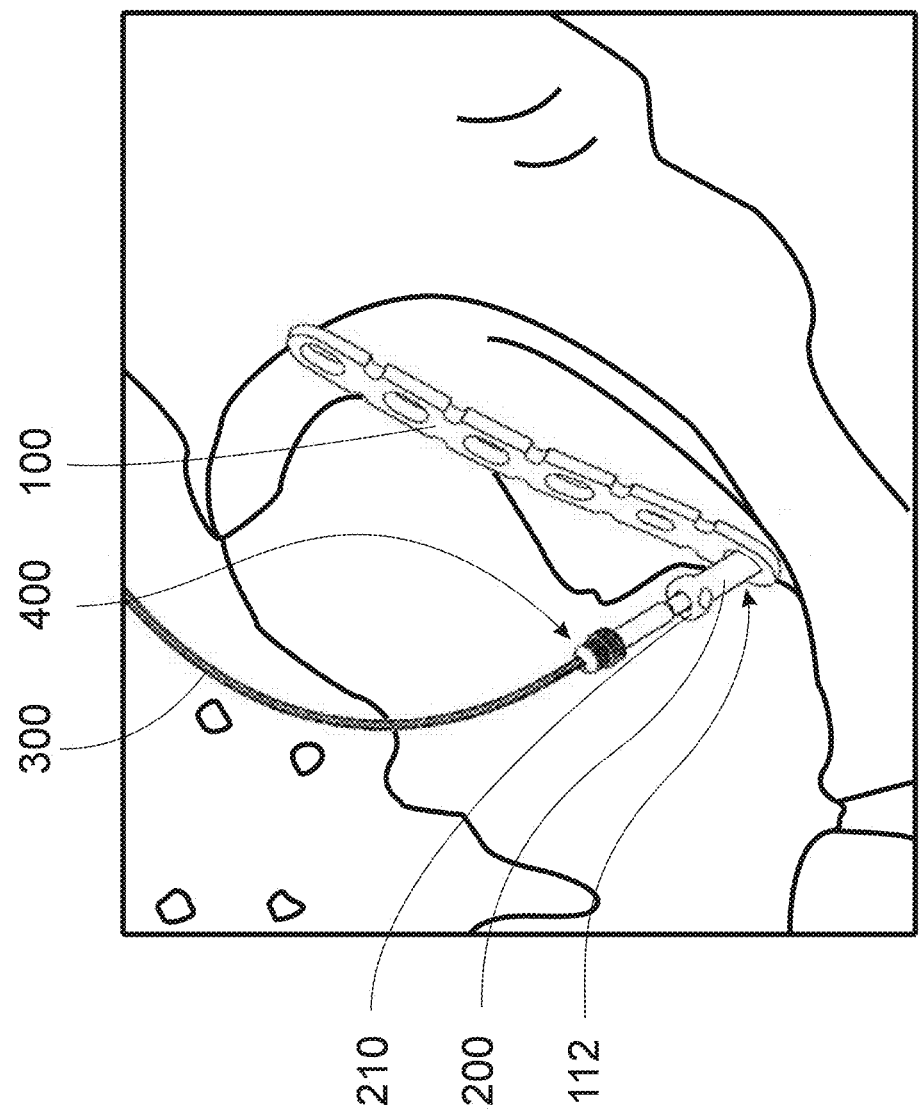
FIG. 24 is a perspective view of the bolt being urged in a medial-to-lateral direction through an opening of the bone plate and into a hole that has been formed in the pelvis.

FIG. 24 illustrates a point in time just prior to introduction of the bolt 200 through the opening 112 of the bone plate 100 and into the drilled hole within the pelvic bone. As the cable 300 is advanced further in the medial-to-lateral direction, the orientation system 400 can urge the bolt 200 into the drilled hole. The pelvic bone can frictionally engage an outer surface of the bolt 200, and the anti-rotation surfaces 220 of the head 210 can interact with the sidewall 114 of the opening 112 to automatically seat against the anti-rotation surfaces 120 defined by the sidewall 114. An image intensifier is used to verify that the bolt 200 is in the proper or desired position within the bone.

The cable 300 can then be moved in the lateral-to-medial direction. As previously discussed, any frictional engagement between the bolt 200 and the plunger 402 can be less than the frictional engagement between the bolt 200 and the bone such that upon application of sufficient force to the cable 300, the insert 410 is removed from the bolt 200 without disrupting the position of the bolt 200 within the bone and the head 210 of the bolt 200 within the opening 112. The cable 300 can be advanced medially by a sufficient amount to remove the orientation system 400 from the patient 600 without pulling the lateral end of the cable 300 into the patient 600 (i.e., while leaving a length of the cable 300 extending laterally from the secondary incision 604).

Figure 25:
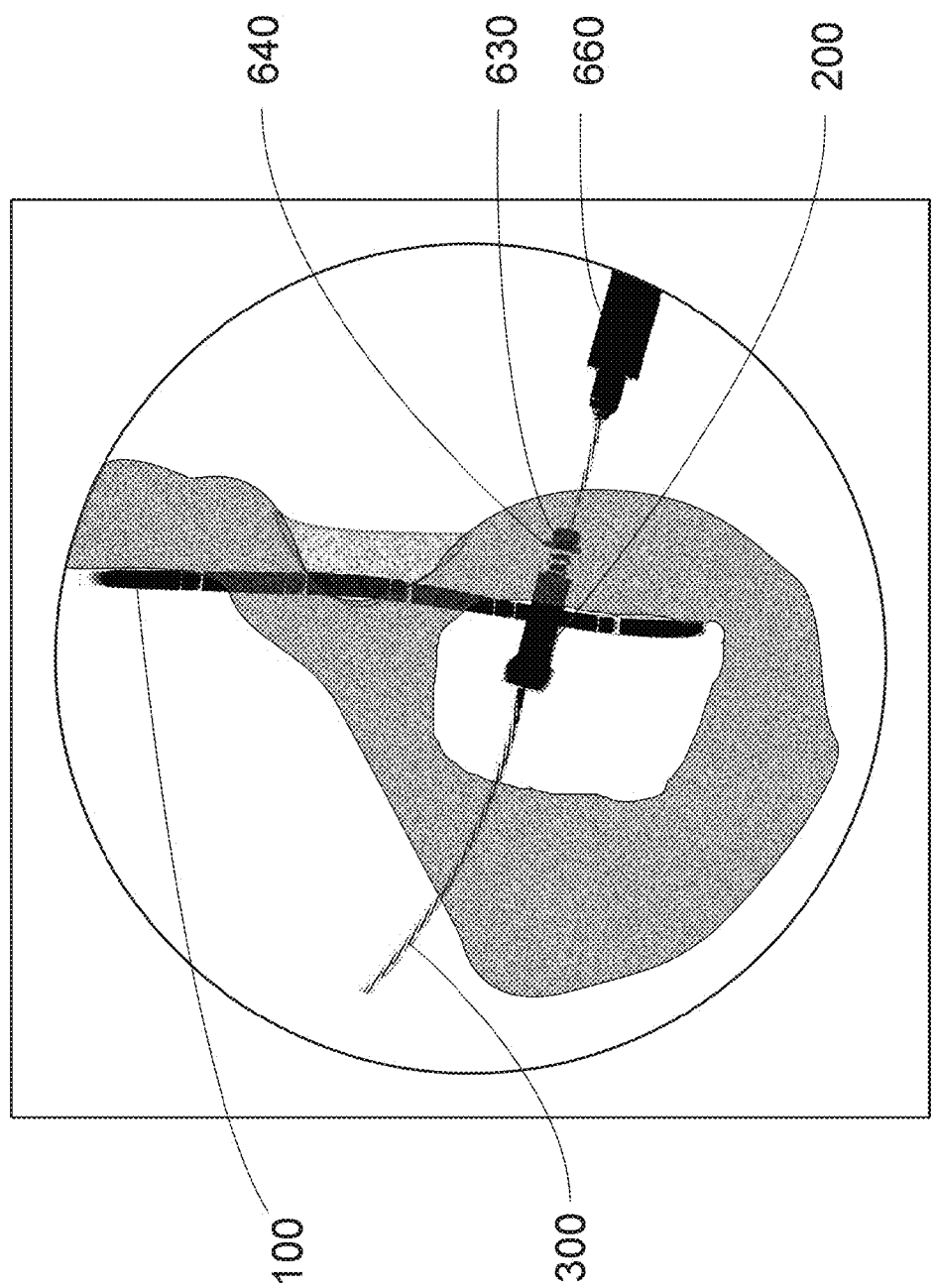
FIG. 25 is a representation of an image intensifier view of the cannulated screw being coupled into the bolt so as to anchor the bone plate to an inner surface of the pelvis.

With reference to FIG. 25, a cannulated screw 630 can be advanced over the lateral end 330 of the cable 300. The screw 630 can be of any suitable variety, including those known in the art and those yet to be devised. A washer 640 can be used with the screw 630 so as to prevent a head of the screw 630 from embedding too far within the pelvic bone. In some instances, the screw 630 may be used without a washer 640. For example, a hole may be drilled through the ischium, which is a tubular bone that can be relatively stiff (e.g., due to its geometry), and can be capable of itself resisting undesirable embedding of the head of the screw 630. In many instances, however, it can be preferable to use a washer 640. In the illustrated embodiment, the screw 630 defines a length of approximately 26 millimeters and a shaft of the screw 630 can define an outer diameter of about 4.5 millimeters. Other length and diameter screws 630 may be used for other patients, or at different locations for the same patient.

The cannulated screw 630 is screwed into the hole that extends through the bone and catches the internal threading 242 (see FIG. 8) of the bolt 200. Tightening of the screw 630 into the bolt can provide a stable anchoring of the bone plate 100. Any suitable device 660 may be used to tighten the screw 630. For example, in some embodiments, the device 660 comprises a screwdriver, a torx driver, or the like. As previously discussed, the anti-rotation surfaces 120, 220 of the bone plate 100 and the bolt 200, respectively, can maintain the head 210 of the bolt 200 within the bone plate 100 and can prevent rotation of the bolt 200 relative to the bone plate 100. An image intensifier view may be used to ensure proper location of the bolt 200 and the screw 630, and may provide views such as that provided in FIG. 25.

Once a first bolt 200 has been anchored in place as desired, one or more additional bolt/screw pairs may be implanted through other openings 112 of the bone plate 100. For example, with reference again to FIG. 1, in some instances, it can be desirable to secure a bolt/screw pair through a topmost opening 112 of the bone plate 100 after a bolt/screw pair has been secured through the lower opening 112. In other arrangements, the second bolt/screw pair can be inserted in an opening 112 that is second or third in line from the upper end of the bone plate 100.

The various steps or stages for inserting the second (and third, fourth, fifth, etc., as desired) bolt/screw pair can follow those discussed above with respect to the first bolt/screw pair. In some embodiments, a third incision (not shown) through which a screw 630 is inserted can be formed at the intersection of a vertical line that has been traced from the anterior and inferior iliac spine and a horizontal line that has been traced from the center of the greater trochanter. In certain of such implementations, a bolt 200 that is about 20 millimeters in length and a cannulated screw that is about 26 millimeters in length and the defines an outer diameter of about 4.5 millimeters may be used for the second bolt/screw pair. In some instances, it may be more desirable to use a washer 640 with the second bolt/screw pair, as the positioning of the pair may be at a less rigid region of the pelvis.

Securing the second screw 630 to the second bolt 200 can cause the bone plate 100 to reduce fractured portions of the pelvis. For example, the head of the second screw 630 can remain at the outer surface of the pelvic bone (in some instances, due to the presence of a washer 640). Accordingly, advancement of the screw 630 into the bolt 200 can cause the bolt 200 to approach the outer surface of the pelvic bone. This likewise can urge the bone plate 100 toward the outer surface of the pelvis, such that the bone plate 100 can directly reduce fractured elements of the pelvis. Stated otherwise, the bone plate 100 can directly act to counter forces that would medially displace pelvic fragments.

Stated in yet another manner, by fixing the bone plate 100 to the pelvic fragments, it is possible to make an indirect reduction via the plate 100, as the plate 100 is placed against the fracture fragments themselves. For certain vertically implanted bone plates 100, the bone plate 100 is positioned distal of the acetabulum and dorsal to acetabulum within the true pelvis, and an attachment of the bone plate 100 can be made through the ischium. As further discussed below, for certain horizontally implanted bone plates 100, the bone plate 100 is positioned dorsal to the acetabulum, and an attachment of the bone plate 100 can be made through the iliopubic rami. Such arrangements can push the quadrilateral wall to its original position. During fixation and/or after fixation has been achieved, an image intensifier can be used to confirm that a fixation is as desired As previously mentioned, sometimes it can be desirable to used more than two bolt/screw pairs by which additional reduction maneuvers may be performed. For example, in some instances where the dorsal column is displaced medially and dorso-cranially, additional bolt/screw pairs can be advantageous. In certain procedures for the reduction of such displacements, a hooked tool or hook device, such as a femoral neck hook (not shown), can be inserted through the primary incision and placed carefully so as to hold the ventral wall of the sciatic notch to pull the fragment ventrally and distally when the bone plate 100 has been fixed to the pelvis with only the first bolt/screw pair (e.g., prior to reduction via the second bolt/screw pair). The hook device reduces the fracture ventrally and distally while the bone plate 100 reduces the fracture laterally as the second bolt/screw pair is tightened. The hook device engages the sciatic notch (ventral part thereof). The reduction is made by pulling the hook device in a distal and ventral direction.

Once all of the desired bolt/screw pairs have been attached to the bone plate 100, the primary (ventral) incision 602 and all secondary (lateral) incisions 604 can be closed in any suitable manner. In some embodiments, a drainage tube may be left in the primary incision 602.

Figure 26:
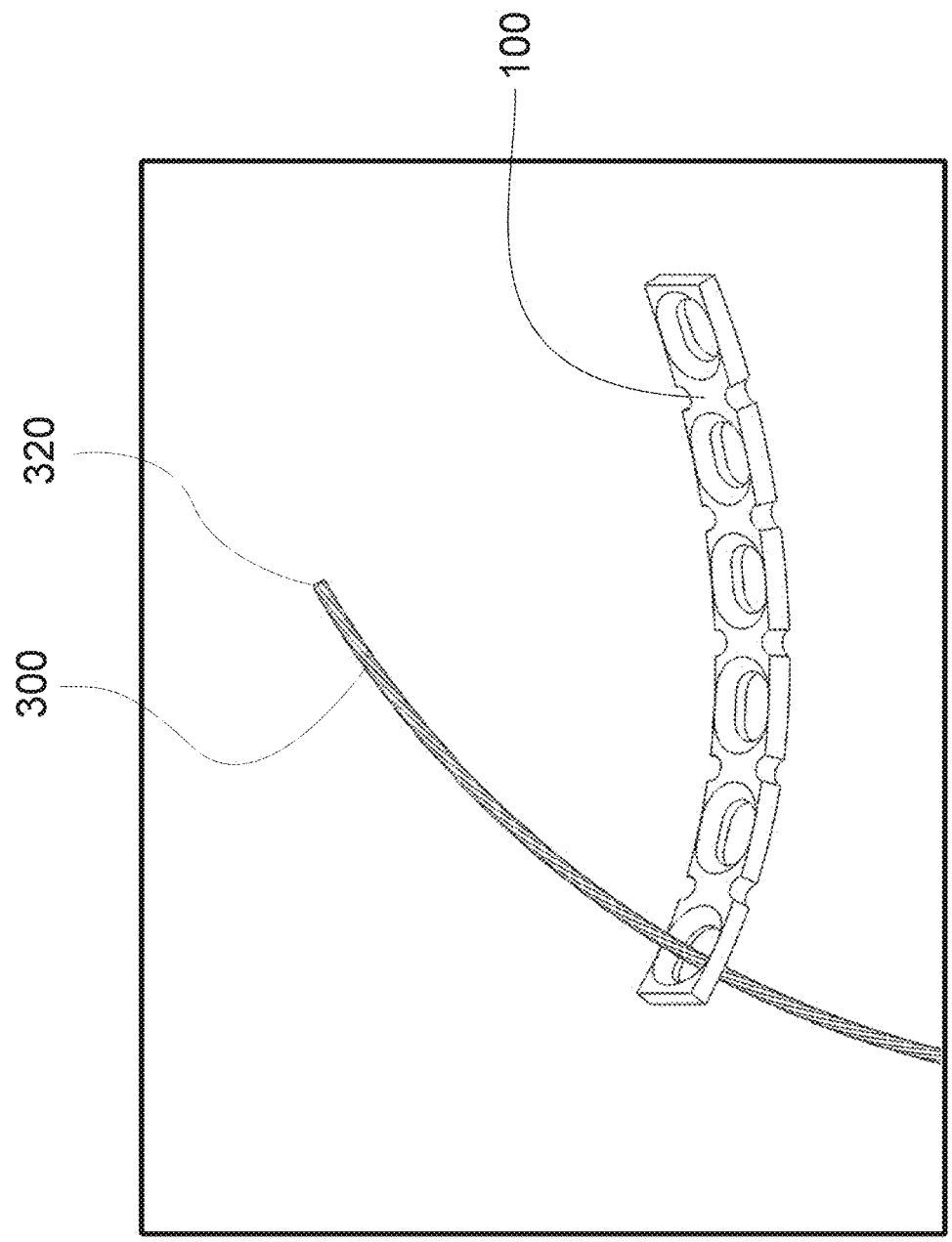
FIG. 26 is a perspective view of the bone plate of FIG. 2 being advanced over the medial end of the cable in an intermediate stage of an alternative method of implanting the bone plate.

With reference to FIG. 26, as an alternative to some portions of the foregoing procedures, the initial insertion of the bone plate 100 through the primary incision 602 and into the true pelvis is done primarily to gain a rough idea of the proper positioning of the plate 100. The bone plate 100 is then removed from the patient 600 for insertion again at a subsequent stage of the procedure. In particular, the bone plate 100 is once again inserted through the primary incision 602 after the hole through the pelvic bone has been formed (e.g., after use of the alignment assembly 500 in creating a hole in the bone). Thus, as shown in FIG. 26, after the medial end 320 of the cable 300 has been pulled through the primary incision 602, the medial end 320 can be inserted through an opening 112 in the bone plate 100. As previously discussed, in some instances, the first opening 112 through which a bolt/screw pair is inserted is the second opening from the bottom or distal end of the bone plate 100, as shown in FIG. 26.

After the bone plate 100 has been positioned over the cable 300, the bolt 200 and the orientation system 400 can be positioned over the cable 300 as described above with respect to FIGS. 23 and 24. Both the bone plate 100 and the bolt 200 can then be advanced carefully through the primary incision site 602 so as to reach the medial opening of the drilled hole, and the bolt 200 is introduced into the hole. As previously discussed, attention may be taken to prevent the bone plate 100 from trapping the obturator nerve and artery.

Figure 27:
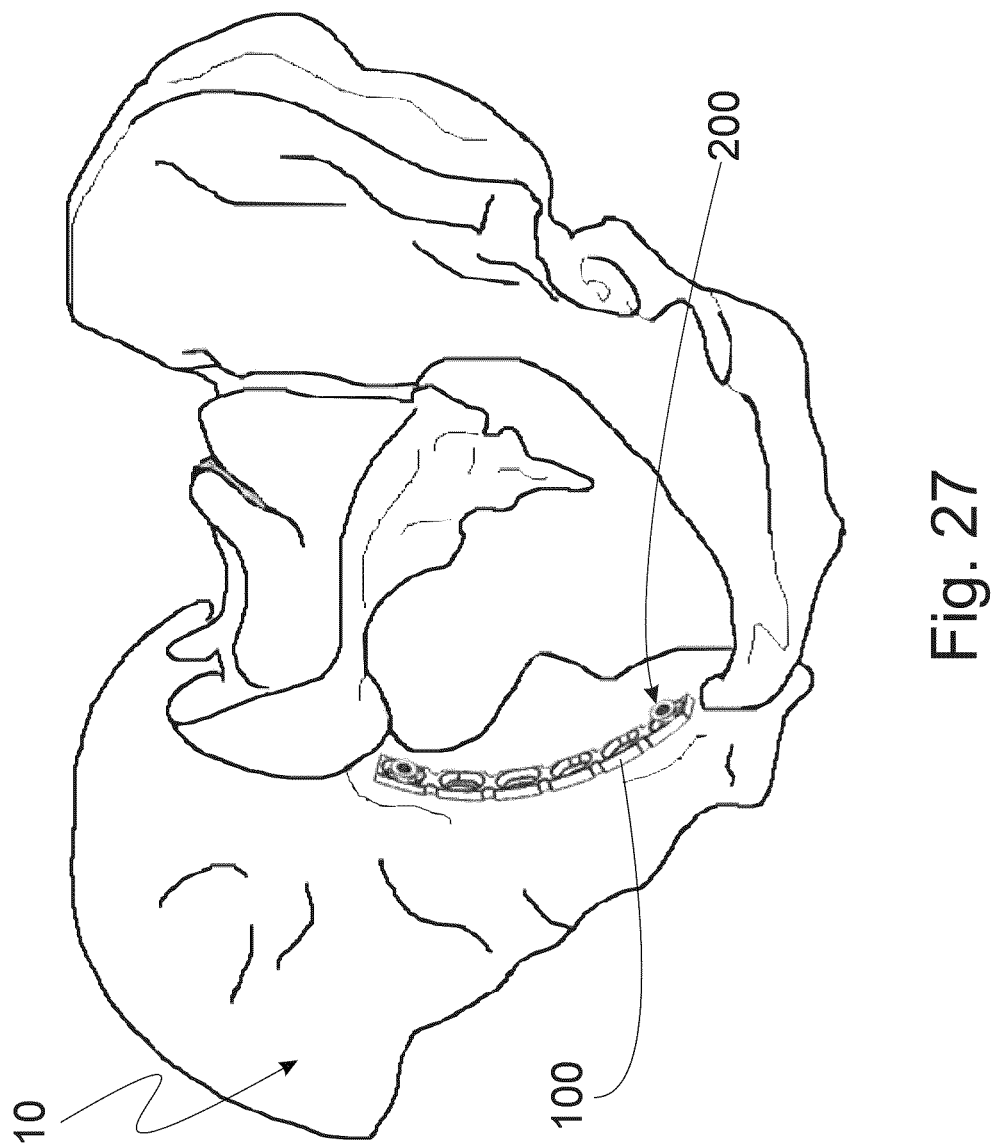
FIG. 27 is a perspective view of another embodiment of a fixation system that includes a bone plate, wherein the bone plate has been implanted in a substantially horizontal orientation so as to span an anterior and a posterior column of a pelvis.

FIG. 27 illustrates another orientation in which the bone plate 100 can be attached to an interior surface of the pelvis 10 using one or more bolts 200 and screws 630. Illustrative methods by which the bone plate 100 can be implanted in this matter are discussed hereafter. Many of the steps or stages of the implantation are similar to those discussed above with respect to the substantially vertically oriented bone plate 100. Accordingly, references to the drawings may be infrequent in the following discussion, but the manners in which the foregoing description of the drawings applies hereafter will be readily apparent to those skilled in the art. Additionally, it is noted that for certain methods of implanting a bone plate 100 in a substantially horizontal orientation, the shorter alignment arm 566 and translational arm 574 can be used with the alignment assembly 500 due to the more shallow regions at which the implantation takes place. In various procedures, one or more ventral bolt/screw pairs are implanted, and then one or more dorsal screw/sex bolt pairs are implanted.

In certain illustrative methods, a bone plate 100 is provided and is shaped as desired. For example, a model of the pelvis may be used to shape the bone plate to the desired contour, and the shaping may be achieved using pliers or a bending press.

The patient is placed in a supine position with a sandbag beneath the ipsilateral renal fossa. A primary incision can be started at a position about 1 centimeter distal to the inguinal line and can be extended proximally about 8 centimeters to about 10 centimeters to a position about 3 centimeters medial to the femoral vessels. In the illustrative method thus described, the primary incision is a vertical incision. Stated otherwise, a primary incision is created in the abdominal region of the patient.

Abdominal muscles and fascia transversalis are sharply dissected vertically. Digitally, the peritoneum is detected and displaced medially. It can be desirable to avoid opening the peritoneum so as to prevent difficulties with the bowel. If accidental damage to the peritoneum occurs, it is desirable to repair the damage immediately (e.g., via suturing).

The internal obturator muscle is digitally identified and is dissected by the surgeon with his or her fingers. The quadrilateral wall, the iliopectineal line, and the fracture fragments (and the displacement of each fragment) are digitally identified. The contoured bone plate 100 is inserted through the primary incision and is presented over the fracture, and may be placed about 1 centimeter distal to the iliopectineal line.

A ventral portion of the iliopubic rami is freed of soft tissue. A guidewire (e.g., 2.5 millimeter outer diameter) is advanced through the desired opening of the bone plate 100 and then through the iliopubic rami in a ventral-to-dorsal direction. The desired opening may be either the opening that is closest to the medial end of the bone plate or the second opening from the medial end, as these positions can easily be accessed via the primary incision. It is possible to use the third or fourth openings from the medial end of the bone plate. Use of the third or fourth openings can be more difficult, as careful attention is taken to avoid important anatomical structures such as femoral vessels and nerves, and as the soft tissue is retracted laterally.

A cannulated drill bit is advanced over the guidewire and a hole is drilled through the bone in the ventral-to-dorsal direction. Two separate approaches are possible for securing the bone plate to the bone using a bolt/screw pair.

In one approach, the guidewire is removed from the drill bit as the drill bit is left in place. The cable 300 is then introduced into a rearward end of the drill bit, advanced through the drill bit in a ventral-to-dorsal direction to a tip of the drill bit such that it extends through the bone and a first opening of the bone plate 100. The cable 300 is then advanced into the pelvis and the medial end 320 thereof is controlled by the surgeon's fingers and is pulled out through the primary incision. The drill bit is then removed through the primary incision. A first sex bolt (e.g., 10 millimeter length) is threaded over the lateral end 330 of the cable 300, is introduced through the primary incision over the cable 300, and is advanced into the drilled hole in a dorsal-to-ventral direction. A first cannulated screw (e.g., 4.5 millimeter outer diameter, from 12 to 16 millimeters in length), along with a washer, is threaded over the medial end 320 of the cable 300, is introduced through the primary incision and advanced over the cable 300, and the screw is eventually advanced into the drilled hole in the bone in a ventral-to-dorsal direction until it touches the tip of the bolt 200. The first cannulated screw 630 is then tightened to the bolt 200.

In a second approach, the guidewire and the drill bit are removed. Then, a first bolt 200 (e.g., 10 millimeters in length) is advanced into the drilled hole in a dorsal-to-ventral direction. A cannulated screw or a standard (non-cannulated) screw (e.g., 4.5 millimeter outer diameter, from 12 to 16 millimeter length) is introduced through the primary incision and advanced into the drilled hole in a ventral-to-dorsal direction. A washer may be used with the screw. The first screw is then tightened.

After attachment of the first bolt/screw pair in either manner just discussed, an second bolt/screw pair is attached to the bone plate 100 so as to reduce the fracture. The alignment arm 566 of the alignment assembly 500 is introduced into the primary incision site and the alignment tip 568 is situated in one of the openings 112 of the bone plate 100. For example, the alignment tip 568 can be placed within the opening that is either the most dorsally (i.e., rearwardly) located or that is one away from the most dorsal opening.

A secondary incision is made at the intersection of a line that extends in an anterior-to-posterior direction, which begins at the anterior and inferior pelvic spine, and a vertical line that extends from the tip of greater trochanter in a proximal direction (e.g., toward a top of the patient). To assist in determining the desired location of the incision, once the alignment arm 566 is in place, as described above, the protection sleeve 580 can be advanced toward the skin until it just touches the skin and makes an impression therein, and then can be retracted away from the skin. The impression can serve as a reference point at which the incision is to be made.

The protection sleeve 530 is then advanced through the secondary incision until contact thereof to bone is sensed. The protection sleeve 530 can include a rounded tip that prevents structural damage that could occur as the sleeve is advanced from the outer surface of the skin into contact with the bone, such as muscles, the gluteal artery, or nerves.

An image intensifier view is used to ensure that the alignment tip 568 is in the appropriate opening of the bone plate 100 (e.g., the opening second from the rear) and also to ensure that the protection sleeve 580 is properly aligned with the alignment tip. A guidewire is inserted through both the protection sleeve 580 and the constriction sleeve 534 of the alignment assembly 500 from the lateral side. Again, at this point, the protection sleeve 580 is located at the intersection of a traced vertical line from the anterior and inferior iliac spine and a horizontal one from the dorsal border of the greater trochanter. The constriction sleeve 534 is then removed from the protection sleeve 534.

Using the guidewire as guide, a drill bit (e.g., 6.0 millimeter outer diameter) is inserted through the protective sleeve 580 to create a drill hole through the bone. After the drill hole has been made through the bone, the guidewire is removed from an interior of the drill bit, while the drill bit is still in place within the protective sleeve 580. The cable 300 is then inserted through the drill bit and caught medially by the surgeon with his or her fingers and is pulled out thorough the primary incision The alignment arm 566 of the alignment assembly 500 is removed from the patient (for example, it can be unthreaded from the guiding arm 502), and the guiding arm 502 is also removed, as is the guidewire; the cannulated drill bit is left in place. The bolt 520 is advanced over the end of the cable 300 that was pulled through the primary incision, with the shaft first and the head side last. In some embodiments, the bolt 520 defines a length of about 20 millimeters.

The orientation system 400 is then advanced over the end of the cable 300 that was pulled through the primary incision, is secured to the cable 300, and the smaller diameter end of the plunger of the orientation system 400 is then inserted into the bolt 200. The cable 300 is then pulled laterally outwardly, or away, from the secondary incision such that the bolt 200 and the orientation system 400 are advanced through the primary incision, into the true pelvis, and eventually into the hole that has been drilled in the pelvis bone structure.

Once the bolt 200 has been pulled into the bone, the cable 300 is pulled in the opposite direction so as to remove the orientation system 400 from the bolt 200. Care may be taken to ensure that the bolt 200 is not inadvertently removed from the bone at this point.

A cannulated screw (e.g., 26 millimeter length, 4.5 millimeter outer diameter) and washer are advanced over the opposite or lateral end of the cable 300 and into the secondary incision. A cannulated screwdriver can be used to engage the screw with the bolt, and as the screw is tightened, the fracture is reduced and a stable fixation is established. An image intensifier can be used to review the reduction and confirm that the desired result has been achieved.

In some cases, additional sex bolt/screw pairs may be introduced into other openings of the bone plate in the manner just described. The primary and secondary incisions are closed in any suitable manner, and a drainage tube may be left in the primary incision.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this Detailed Description are hereby expressly incorporated into this Detailed Description, with each claim standing on its own as a separate embodiment. This disclosure includes all permutations of the independent claims with their dependent claims. Recitation in the claims of the term "first" with respect to a feature or element does not necessarily imply the existence of a second or additional such feature or element. Elements specifically recited in means-plus-function format, if any, are intended to be construed in accordance with 35 U.S.C. §112 ¶ 6. Embodiments of the invention in which an exclusive property or privilege is claimed are defined as follows.

The invention claimed is:

1. A system for repairing acetabulum fractures, the system comprising:
a bone plate configured to be fixed into a non-planar portion of the pelvis in a direction from the bone to the bone plate, such bone plate comprising an elongated body in a longitudinal direction, the elongated body having an upper face, a lower face opposite of the upper face; and opposing side faces that extend between the upper face and the lower face, such opposite side faces comprising a plurality of opposing pairs of notches configured to allow lateral flexion of the bone plate; a plurality of openings aligned along a longitudinal axis of the bone plate and which extend through the upper face and the lower face of the elongated body, each of the plurality of openings being at least partially defined by a sidewall that extends from the upper face to the lower face of the body each sidewall having a surface that is substantially planar and is angled inwardly in a direction from the upper face toward the lower face of the body of the bone plate to prevent rotation of the sex bolt head within the opening; and
a sex bolt without external thread comprising a hollow shaft sized to pass through any of said plurality of openings of the elongated body of the bone plate, the hollow shaft defining an opening at a distal end thereof and comprising internal threads that are configured to cooperatively couple with external threads of a screw, the hollow shaft further defining a longitudinal axis; and a head sized to cooperate with the sidewall of any of said plurality of openings to prevent the sex bolt from passing completely through an opening of any of said plurality of openings when the hollow shaft of the sex bolt is advanced through the opening in a distal direction and into a pelvis through an interior surface of the pelvis, and such that the head of the sex bolt is configured to permit translation relative to the sidewall when the head of the bolt is within the sidewall to allow three dimensional fracture fragment reduction, the head comprising a surface that is configured to cooperate with the sidewall to prevent the sex bolt from rotating about the longitudinal axis as a screw is advanced through the opening at the distal end of the sex bolt and is coupled with the internal threads of the sex bolt.

2. The system of claim 1, wherein each of the plurality of openings is elongated such that the head of the sex bolt is permitted to translate relative to the sidewall when the head of the sex bolt is within the sidewall.

3. The system of claim 1, wherein the plurality of openings are elongated in the longitudinal direction along which the body of the bone plate is elongated.

4. The system of claim 1, wherein the sidewall comprises a pair of substantially planar surfaces that slope inwardly in a direction away from the upper face and toward the lower face of the body of the bone plate.

5. The system of claim 2, wherein the head of the sex bolt is configured to cooperate with the sidewall to prevent translation of the sex bolt therein, once a screw has been advanced sufficiently far into the sex bolt to secure the bone plate to a bone.

6. The system of claim 5, wherein the head of the sex bolt comprises a pair of substantially planar surfaces, which are complementary to the substantially planar surfaces of the sidewall of the plurality of openings.

7. The system of claim 1, wherein each pair of notches is extending inwardly toward each other and is positioned longitudinally between adjacent openings to diminish plate stiffness allowing the lateral plate flexion in order to contour the plate to be adapted to bone anatomy in sagittal, frontal and coronal planes.

8. The system of claim 1, further comprising a cannulated screw configured to couple with the sex bolt, so that the while cannulated screw is being tightened into the sex bolt, the screw produces traction to the sex bolt lagging it, producing transverse compression of acetabular fracture fragments, acting as a lag screw.

9. The system of claim 1, comprising a bone plate comprising:
an elongated body in a longitudinal direction, the body having an upper face, a lower face opposite the upper face, and opposing side faces that extend between the upper and lower faces;

a plurality of openings that extend through the upper and lower faces of the elongated body, each opening being defined by a sidewall that extends from the upper face to the lower face of the body, wherein each sidewall comprises a surface that is configured to prevent rotation of a head of a sex bolt within the opening; and a plurality of opposing pairs of notches defined by the side faces of the body, each pair extending inwardly toward each other and positioned longitudinally between adjacent openings.

10. The system of claim 9, wherein each opening of the bone plate is elongated in the longitudinal direction so as to permit a head of a sex bolt to translate longitudinally therein prior to tightening of the sex bolt.

11. The system of claim 9, wherein the substantially planar surface extends from the upper face to a position above the lower face that is no more than about ⅓ of a distance between the upper and lower faces.

12. The system of claim 9, wherein the plurality of openings are aligned along a longitudinal axis of the bone plate.

* * * * *